(12) United States Patent
Casey et al.

(10) Patent No.: US 11,839,725 B2
(45) Date of Patent: Dec. 12, 2023

(54) CLOT RETRIEVAL DEVICE WITH OUTER SHEATH AND INNER CATHETER

(71) Applicant: NEURAVI LIMITED, Galway (IE)

(72) Inventors: Brendan Casey, Galway (IE); Karl Keating, Galway (IE); Ronald Kelly, Galway (IE); David Vale, Galway (IE)

(73) Assignee: NEURAVI LIMITED, Galway (IE)

( * ) Notice: Subject to any disclaimer, the term of this patent is extended or adjusted under 35 U.S.C. 154(b) by 317 days.

(21) Appl. No.: 17/103,302

(22) Filed: Nov. 24, 2020

(65) Prior Publication Data

US 2021/0154433 A1 May 27, 2021

Related U.S. Application Data

(60) Provisional application No. 62/941,366, filed on Nov. 27, 2019.

(51) Int. Cl.
*A61B 17/221* (2006.01)
*A61M 25/01* (2006.01)
*A61M 25/04* (2006.01)

(52) U.S. Cl.
CPC ....... *A61M 25/0133* (2013.01); *A61B 17/221* (2013.01); *A61M 25/04* (2013.01);
(Continued)

(58) Field of Classification Search
CPC ............ A61B 17/221; A61B 17/22031; A61B 2017/2215; A61B 2017/2212;
(Continued)

(56) References Cited

U.S. PATENT DOCUMENTS

| 4,243,040 A | 1/1981 | Beecher |
| 4,324,262 A | 4/1982 | Hall |

(Continued)

FOREIGN PATENT DOCUMENTS

| CN | 1658920 A | 8/2005 |
| CN | 1972728 A | 5/2007 |

(Continued)

OTHER PUBLICATIONS

US 6,348,062 B1, 02/2002, Hopkins (withdrawn)
(Continued)

*Primary Examiner* — Majid Jamialahmadi
(74) *Attorney, Agent, or Firm* — TROUTMAN PEPPER HAMILTON SANDERS LLP

(57) ABSTRACT

A device for retrieving an obstruction in a blood vessel can have an outer sheath with a distal end, a proximal end, a proximal luer encompassing the proximal end, and an internal lumen extending proximal of the distal end and terminating within the proximal luer; and an inner funnel catheter within the outer sheath comprising an expanding distal tip, a proximal end, a distal end located at the distal tip, a proximal luer encompassing the proximal end, and an internal lumen extending proximal of the distal end and terminating at the luer. The outer sheath and inner funnel catheter can be capable of moving telescopically with respect to each other. In some examples, a slider mechanism or rotating knob located on one of the proximal luers can be used to actuate the relative motion.

17 Claims, 14 Drawing Sheets

(52) U.S. Cl.
CPC ............... *A61B 2017/2215* (2013.01); *A61M 2025/015* (2013.01); *A61M 2025/0175* (2013.01); *A61M 2210/0625* (2013.01)

(58) Field of Classification Search
CPC ........... A61B 2017/22034; A61B 2017/22035; A61M 2025/0175
See application file for complete search history.

(56) References Cited

U.S. PATENT DOCUMENTS

| | | | |
|---|---|---|---|
| 4,351,342 A | 9/1982 | Wiita et al. | |
| 4,575,371 A | 3/1986 | Nordqvist et al. | |
| 4,592,356 A | 6/1986 | Gutierrez | |
| 4,719,924 A | 1/1988 | Crittenden et al. | |
| 4,738,666 A | 4/1988 | Fuqua | |
| 4,767,404 A | 8/1988 | Renton | |
| 4,793,348 A | 12/1988 | Palmaz | |
| 4,873,978 A | 10/1989 | Ginsburg | |
| 5,011,488 A | 4/1991 | Ginsburg | |
| 5,092,839 A | 3/1992 | Kipperman | |
| 5,102,415 A | 4/1992 | Guenther et al. | |
| 5,122,136 A | 6/1992 | Guglielmi et al. | |
| 5,123,840 A | 6/1992 | Nates | |
| 5,171,233 A | 12/1992 | Amplatz | |
| 5,234,437 A | 8/1993 | Sepetka | |
| 5,256,144 A | 10/1993 | Kraus et al. | |
| 5,261,916 A | 11/1993 | Engelson | |
| 5,372,124 A | 12/1994 | Takayama et al. | |
| 5,385,562 A | 1/1995 | Adams | |
| 5,387,219 A | 2/1995 | Rappe | |
| 5,387,226 A | 2/1995 | Miraki | |
| 5,396,902 A | 3/1995 | Brennen et al. | |
| 5,449,372 A | 9/1995 | Schmaltz | |
| 5,520,651 A | 5/1996 | Sutcu | |
| 5,538,512 A | 7/1996 | Zenzon et al. | |
| 5,549,626 A | 8/1996 | Miller et al. | |
| 5,558,652 A | 9/1996 | Henke | |
| 5,601,600 A | 2/1997 | Ton | |
| 5,609,627 A | 3/1997 | Goicoechea et al. | |
| 5,624,461 A | 4/1997 | Mariant | |
| 5,639,277 A | 6/1997 | Mariant | |
| 5,645,558 A | 7/1997 | Horton | |
| 5,658,296 A | 8/1997 | Bates | |
| 5,662,671 A | 9/1997 | Barbut | |
| 5,695,519 A | 12/1997 | Summer et al. | |
| 5,709,704 A | 1/1998 | Nott et al. | |
| 5,713,853 A | 2/1998 | Clark | |
| 5,728,078 A | 3/1998 | Powers, Jr. | |
| 5,769,871 A | 6/1998 | Mers Kelly | |
| 5,779,716 A | 7/1998 | Cano | |
| 5,810,874 A | 9/1998 | Lefebvre | |
| 5,814,064 A | 9/1998 | Danniel et al. | |
| 5,827,304 A | 10/1998 | Hart | |
| 5,846,251 A | 12/1998 | Hart | |
| 5,855,598 A | 1/1999 | Pinchuk | |
| 5,893,869 A | 4/1999 | Barnhart et al. | |
| 5,895,398 A | 4/1999 | Wensel | |
| 5,897,567 A | 4/1999 | Ressemann | |
| 5,904,698 A | 5/1999 | Thomas et al. | |
| 5,911,725 A | 6/1999 | Boury | |
| 5,935,139 A | 8/1999 | Bates | |
| 5,938,645 A | 8/1999 | Gordon | |
| 5,947,995 A | 9/1999 | Samuels | |
| 5,968,057 A | 10/1999 | Taheri | |
| 5,971,938 A | 10/1999 | Hart et al. | |
| 5,997,939 A | 12/1999 | Moechnig et al. | |
| 6,022,343 A | 2/2000 | Johnson et al. | |
| 6,063,113 A | 5/2000 | Kavteladze | |
| 6,066,149 A | 5/2000 | Samson et al. | |
| 6,066,158 A | 5/2000 | Engelson | |
| 6,093,196 A | 7/2000 | Okada | |
| 6,093,199 A | 7/2000 | Brown et al. | |
| 6,096,053 A | 8/2000 | Bates | |
| 6,099,534 A | 8/2000 | Bates | |
| 6,102,932 A | 8/2000 | Kurz | |
| 6,106,548 A | 8/2000 | Roubin et al. | |
| 6,129,739 A | 10/2000 | Khosravi | |
| 6,142,957 A | 11/2000 | Diamond et al. | |
| 6,146,396 A | 11/2000 | Kónya et al. | |
| 6,146,404 A | 11/2000 | Kim | |
| 6,165,194 A | 12/2000 | Denardo | |
| 6,165,199 A | 12/2000 | Barbut | |
| 6,168,604 B1 | 1/2001 | Cano | |
| 6,168,622 B1 | 1/2001 | Mazzocchi | |
| 6,174,318 B1 | 1/2001 | Bates et al. | |
| 6,179,861 B1 | 1/2001 | Khosravi | |
| 6,203,561 B1 | 3/2001 | Ramee | |
| 6,214,026 B1 | 4/2001 | Lepak | |
| 6,221,006 B1 | 4/2001 | Dubrul | |
| 6,238,412 B1 | 5/2001 | Dubrul | |
| 6,245,087 B1 | 6/2001 | Addis | |
| 6,251,122 B1 | 6/2001 | Tsukernik | |
| 6,254,571 B1 | 7/2001 | Hart | |
| 6,264,663 B1 | 7/2001 | Cano | |
| 6,306,163 B1 | 10/2001 | Fitz | |
| 6,309,379 B1 | 10/2001 | Willard | |
| 6,312,444 B1 | 11/2001 | Barbut | |
| 6,315,778 B1 | 11/2001 | Gambale et al. | |
| 6,325,819 B1 | 12/2001 | Pavcnik et al. | |
| 6,334,864 B1 | 1/2002 | Amplatz et al. | |
| 6,336,934 B1 | 1/2002 | Gilson et al. | |
| 6,348,056 B1 | 2/2002 | Bates | |
| 6,350,271 B1 | 2/2002 | Kurz et al. | |
| 6,361,545 B1 | 3/2002 | Macoviak | |
| 6,371,963 B1 | 4/2002 | Nishtala et al. | |
| 6,375,668 B1 | 4/2002 | Gifford et al. | |
| 6,383,205 B1 | 5/2002 | Samson et al. | |
| 6,383,206 B1 | 5/2002 | Gillick | |
| 6,391,037 B1 | 5/2002 | Greenhalgh | |
| 6,402,771 B1 | 6/2002 | Palmer | |
| 6,409,683 B1 | 6/2002 | Fonseca et al. | |
| 6,416,541 B2 | 7/2002 | Denardo | |
| 6,425,909 B1 | 7/2002 | Dieck et al. | |
| 6,432,122 B1 | 8/2002 | Gilson et al. | |
| 6,436,112 B2 | 8/2002 | Wensel | |
| 6,458,139 B1 | 10/2002 | Palmer | |
| 6,346,116 B1 | 11/2002 | Brooks et al. | |
| 6,485,497 B2 | 11/2002 | Wensel | |
| 6,485,501 B1 | 11/2002 | Green | |
| 6,485,502 B2 | 11/2002 | Don Michael | |
| 6,511,492 B1 | 1/2003 | Rosenbluth | |
| 6,517,551 B1 | 2/2003 | Driskill | |
| 6,520,934 B1 | 2/2003 | Lee et al. | |
| 6,520,951 B1 | 2/2003 | Carrillo, Jr. | |
| 6,530,935 B2 | 3/2003 | Wensel | |
| 6,530,939 B1 | 3/2003 | Hopkins | |
| 6,540,768 B1 | 4/2003 | Diaz et al. | |
| 6,544,279 B1 | 4/2003 | Hopkins | |
| 6,551,341 B2 | 4/2003 | Boylan et al. | |
| 6,551,342 B1 | 4/2003 | Shen et al. | |
| 6,575,997 B1 | 6/2003 | Palmer et al. | |
| 6,582,448 B1 | 6/2003 | Boyle | |
| 6,585,756 B1 | 7/2003 | Strecker | |
| 6,589,265 B1 | 7/2003 | Palmer et al. | |
| 6,592,607 B1 | 7/2003 | Palmer et al. | |
| 6,592,616 B1 | 7/2003 | Stack | |
| 6,602,271 B2 | 8/2003 | Adams | |
| 6,602,272 B2 | 8/2003 | Boylan et al. | |
| 6,605,102 B1 | 8/2003 | Mazzocchi et al. | |
| 6,610,077 B1 | 8/2003 | Hancock et al. | |
| 6,616,679 B1 | 9/2003 | Khosravi | |
| 6,632,241 B1 | 10/2003 | Hancock et al. | |
| 6,638,245 B2 | 10/2003 | Miller | |
| 6,638,293 B1 | 10/2003 | Makower et al. | |
| 6,641,590 B1 | 11/2003 | Palmer et al. | |
| 6,652,555 B1 | 11/2003 | VanTassel et al. | |
| 6,656,218 B1 | 12/2003 | Denardo et al. | |
| 6,660,021 B1 | 12/2003 | Palmer et al. | |
| 6,663,650 B2 | 12/2003 | Sepetka | |
| 6,673,089 B1 | 1/2004 | Yassour et al. | |
| 6,685,722 B1 | 2/2004 | Rosenbluth | |
| 6,692,504 B2 | 2/2004 | Kurz et al. | |
| 6,692,508 B2 | 2/2004 | Wensel | |

(56) References Cited

U.S. PATENT DOCUMENTS

| | | |
|---|---|---|
| 6,692,509 B2 | 2/2004 | Wensel |
| 6,702,782 B2 | 3/2004 | Miller |
| 6,712,834 B2 | 3/2004 | Yassour et al. |
| 6,726,701 B2 | 4/2004 | Gilson et al. |
| 6,726,703 B2 | 4/2004 | Broome et al. |
| 6,730,104 B1 | 5/2004 | Sepetka |
| 6,824,545 B2 | 11/2004 | Sepetka |
| 6,855,155 B2 | 2/2005 | Denardo et al. |
| 6,878,163 B2 | 4/2005 | Denardo et al. |
| 6,890,340 B2 | 5/2005 | Duane |
| 6,913,612 B2 | 7/2005 | Palmer |
| 6,913,618 B2 | 7/2005 | Denardo et al. |
| 6,953,472 B2 | 10/2005 | Palmer et al. |
| 6,989,019 B2 | 1/2006 | Mazzocchi |
| 6,989,021 B2 | 1/2006 | Bosma et al. |
| 6,994,718 B2 | 2/2006 | Groothuis et al. |
| 6,997,939 B2 | 2/2006 | Linder |
| 7,004,954 B1 | 2/2006 | Voss et al. |
| 7,004,955 B2 | 2/2006 | Shen |
| 7,004,956 B2 | 2/2006 | Palmer |
| 7,008,434 B2 | 3/2006 | Kurz et al. |
| 7,033,376 B2 | 4/2006 | Tsukernik |
| 7,041,116 B2 | 5/2006 | Goto |
| 7,048,758 B2 | 5/2006 | Boyle |
| 7,058,456 B2 | 6/2006 | Pierce |
| 7,063,707 B2 | 6/2006 | Bose |
| 7,153,320 B2 | 12/2006 | Euteneuer et al. |
| 7,175,655 B1 | 2/2007 | Malaei |
| 7,179,273 B1 | 2/2007 | Palmer et al. |
| 7,220,269 B1 | 5/2007 | Ansel |
| 7,220,271 B2 | 5/2007 | Clubb |
| 7,226,464 B2 | 6/2007 | Garner et al. |
| 7,229,472 B2 | 6/2007 | DePalma et al. |
| 7,232,462 B2 | 6/2007 | Schaeffer |
| 7,288,112 B2 | 10/2007 | Denardo et al. |
| 7,306,618 B2 | 12/2007 | Demond |
| 7,316,692 B2 | 1/2008 | Huffmaster |
| 7,323,001 B2 | 1/2008 | Cubb |
| 7,331,976 B2 | 2/2008 | McGuckin, Jr. et al. |
| 7,344,550 B2 | 3/2008 | Carrison et al. |
| 7,399,308 B2 | 7/2008 | Borillo et al. |
| 7,410,491 B2 | 8/2008 | Hopkins |
| 7,452,496 B2 | 11/2008 | Brady et al. |
| 7,491,215 B2 | 2/2009 | Vale et al. |
| 7,491,216 B2 | 2/2009 | Brady |
| 7,510,565 B2 | 3/2009 | Gilson et al. |
| 7,534,252 B2 | 5/2009 | Sepetka |
| 7,556,636 B2 | 7/2009 | Mazzocchi |
| 7,582,111 B2 | 9/2009 | Krolik et al. |
| 7,594,926 B2 | 9/2009 | Linder |
| 7,604,649 B2 | 10/2009 | McGuckin et al. |
| 7,618,434 B2 | 11/2009 | Santra et al. |
| 7,662,165 B2 | 2/2010 | Gilson et al. |
| 7,670,356 B2 | 3/2010 | Mazzocchi |
| 7,691,121 B2 | 4/2010 | Rosenbluth |
| 7,691,124 B2 | 4/2010 | Balgobin |
| 7,708,770 B2 | 5/2010 | Linder |
| 7,736,385 B2 | 6/2010 | Agnew |
| 7,766,934 B2 | 8/2010 | Pal |
| 7,771,452 B2 | 8/2010 | Pal |
| 7,780,694 B2 | 8/2010 | Palmer |
| 7,780,696 B2 | 8/2010 | Daniel et al. |
| 7,819,893 B2 | 10/2010 | Brady et al. |
| 7,828,815 B2 | 11/2010 | Mazzocchi |
| 7,846,176 B2 | 11/2010 | Mazzocchi |
| 7,846,175 B2 | 12/2010 | Bonnette et al. |
| 7,850,708 B2 | 12/2010 | Pal |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi |
| 7,927,349 B2 | 4/2011 | Brady et al. |
| 7,927,784 B2 | 4/2011 | Simpson |
| 7,931,659 B2 | 4/2011 | Bose et al. |
| 7,998,165 B2 | 8/2011 | Huffmaster |
| 8,002,822 B2 | 8/2011 | Glocker et al. |
| 8,021,379 B2 | 9/2011 | Thompson et al. |
| 8,021,380 B2 | 9/2011 | Thompson et al. |
| 8,043,326 B2 | 10/2011 | Hancock et al. |
| 8,048,151 B2 | 11/2011 | O'Brien et al. |
| 8,052,640 B2 | 11/2011 | Fiorella et al. |
| 8,057,497 B1 | 11/2011 | Raju et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,935 B2 | 1/2012 | Rosenbluth et al. |
| 8,109,941 B2 | 2/2012 | Richardson |
| 8,118,829 B2 | 2/2012 | Carrison et al. |
| 8,123,769 B2 | 2/2012 | Osborne |
| 8,137,377 B2 | 3/2012 | Palmer et al. |
| 8,142,422 B2 | 3/2012 | Makower et al. |
| 8,142,442 B2 | 3/2012 | Palmer et al. |
| 8,182,508 B2 | 5/2012 | Magnuson et al. |
| 8,187,298 B2 | 5/2012 | Pal |
| 8,246,641 B2 | 8/2012 | Osborne et al. |
| 8,246,672 B2 | 8/2012 | Osborne |
| 8,252,017 B2 | 8/2012 | Paul, Jr. et al. |
| 8,252,018 B2 | 8/2012 | Valaie |
| 8,357,178 B2 | 1/2013 | Grandfield et al. |
| 8,357,179 B2 | 1/2013 | Grandfield et al. |
| 8,357,893 B2 | 1/2013 | Xu et al. |
| 8,361,095 B2 | 1/2013 | Osborne |
| 8,366,663 B2 | 2/2013 | Fiorella et al. |
| 8,372,133 B2 | 2/2013 | Douk et al. |
| 8,382,742 B2 | 2/2013 | Hermann et al. |
| 8,409,215 B2 | 4/2013 | Sepetka et al. |
| 8,419,748 B2 | 4/2013 | Valaie |
| 8,460,312 B2 | 6/2013 | Bose et al. |
| 8,460,313 B2 | 6/2013 | Huffmaster |
| 8,486,104 B2 | 7/2013 | Samson et al. |
| 8,529,596 B2 | 9/2013 | Grandfield et al. |
| 8,574,262 B2 | 11/2013 | Ferrera et al. |
| 8,579,915 B2 | 11/2013 | French et al. |
| 8,585,643 B2 | 11/2013 | Vo et al. |
| 8,585,713 B2 | 11/2013 | Ferrera et al. |
| 8,608,761 B2 | 12/2013 | Osborne et al. |
| 8,679,142 B2 | 3/2014 | Slee et al. |
| 8,696,622 B2 | 4/2014 | Fiorella et al. |
| 8,702,652 B2 | 4/2014 | Fiorella et al. |
| 8,702,724 B2 | 4/2014 | Olsen et al. |
| 8,784,434 B2 | 7/2014 | Rosenbluth et al. |
| 8,784,441 B2 | 7/2014 | Rosenbluth et al. |
| 8,795,305 B2 | 8/2014 | Grandfield et al. |
| 8,795,317 B2 | 8/2014 | Grandfield et al. |
| 8,795,345 B2 | 8/2014 | Grandfield et al. |
| 8,814,892 B2 | 8/2014 | Galdonik et al. |
| 8,814,925 B2 | 8/2014 | Hilaire et al. |
| 8,900,265 B1 | 12/2014 | Ulm, III |
| 8,939,991 B2 | 1/2015 | Krolik et al. |
| 8,945,143 B2 | 2/2015 | Ferrera et al. |
| 8,945,172 B2 | 2/2015 | Ferrera et al. |
| 8,968,330 B2 | 3/2015 | Rosenbluth et al. |
| 9,039,749 B2 | 5/2015 | Shrivastava et al. |
| 9,072,537 B2 | 7/2015 | Grandfield et al. |
| 9,113,936 B2 | 8/2015 | Palmer et al. |
| 9,119,656 B2 | 9/2015 | Bose et al. |
| 9,138,307 B2 | 9/2015 | Valaie |
| 9,149,609 B2 | 10/2015 | Ansel et al. |
| 9,155,552 B2 | 10/2015 | Ulm, III |
| 9,161,766 B2 | 10/2015 | Slee et al. |
| 9,173,668 B2 | 11/2015 | Ulm, III |
| 9,186,487 B2 | 11/2015 | Dubrul et al. |
| 9,198,687 B2 | 12/2015 | Fulkerson et al. |
| 9,204,887 B2 | 12/2015 | Cully et al. |
| 9,221,132 B2 | 12/2015 | Bowman |
| 9,232,992 B2 | 1/2016 | Heidner |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |

(56) References Cited

U.S. PATENT DOCUMENTS

| | | |
|---|---|---|
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,635 B2 | 5/2017 | Vale et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Paterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 10,028,759 B2 | 7/2018 | Wallace et al. |
| 10,149,692 B2 | 12/2018 | Turjman et al. |
| 10,265,086 B2 | 4/2019 | Vale |
| 10,610,668 B2 | 4/2020 | Burkholz et al. |
| 10,716,915 B2 | 7/2020 | Ogle et al. |
| 10,835,271 B2 | 11/2020 | Ma |
| 11,076,879 B2 | 8/2021 | Yee et al. |
| 2001/0001315 A1 | 5/2001 | Bates |
| 2001/0011182 A1 | 8/2001 | Dubrul et al. |
| 2001/0016755 A1 | 8/2001 | Addis |
| 2001/0041899 A1 | 11/2001 | Foster |
| 2001/0044598 A1 | 11/2001 | Parodi |
| 2001/0044634 A1 | 11/2001 | Don Michael et al. |
| 2001/0051810 A1 | 12/2001 | Dubrul |
| 2002/0002383 A1 | 1/2002 | Sepetka et al. |
| 2002/0016609 A1 | 2/2002 | Wensel |
| 2002/0022859 A1 | 2/2002 | Hogendijk |
| 2002/0026211 A1 | 2/2002 | Khosravi |
| 2002/0049468 A1 | 4/2002 | Streeter |
| 2002/0052620 A1 | 5/2002 | Barvut |
| 2002/0068954 A1 | 6/2002 | Foster |
| 2002/0072764 A1 | 6/2002 | Sepetka |
| 2002/0082558 A1 | 6/2002 | Samson |
| 2002/0091407 A1 | 7/2002 | Zadno-Azizi et al. |
| 2002/0095171 A1 | 7/2002 | Belef |
| 2002/0123765 A1 | 9/2002 | Sepetka |
| 2002/0143362 A1 | 10/2002 | Macoviak et al. |
| 2002/0156455 A1 | 10/2002 | Barbut |
| 2002/0161393 A1 | 10/2002 | Demond |
| 2002/0165576 A1 | 11/2002 | Boyle et al. |
| 2002/0173819 A1 | 11/2002 | Leeflang et al. |
| 2002/0177800 A1 | 11/2002 | Bagaoisan et al. |
| 2002/0188276 A1 | 12/2002 | Evans |
| 2003/0004536 A1 | 1/2003 | Boylan et al. |
| 2003/0004538 A1 | 1/2003 | Secrest |
| 2003/0004542 A1 | 1/2003 | Wensel |
| 2003/0009146 A1 | 1/2003 | Muni |
| 2003/0009191 A1 | 1/2003 | Wensel |
| 2003/0023204 A1 | 1/2003 | Vo et al. |
| 2003/0040769 A1 | 2/2003 | Kelley et al. |
| 2003/0040772 A1 | 2/2003 | Hyodoh et al. |
| 2003/0050663 A1 | 3/2003 | Khachin |
| 2003/0105484 A1 | 6/2003 | Boyle et al. |
| 2003/0125798 A1 | 7/2003 | Matrin |
| 2003/0130682 A1 | 7/2003 | Broome et al. |
| 2003/0144687 A1 | 7/2003 | Brady et al. |
| 2003/0144689 A1 | 7/2003 | Brady et al. |
| 2003/0153940 A1 | 8/2003 | Nohilly et al. |
| 2003/0153943 A1 | 8/2003 | Michael et al. |
| 2003/0153944 A1 | 8/2003 | Phung |
| 2003/0163064 A1 | 8/2003 | Vrba |
| 2003/0163158 A1 | 8/2003 | Wlite |
| 2003/0171769 A1 | 9/2003 | Barbut |
| 2003/0176884 A1 | 9/2003 | Berrada et al. |
| 2003/0187495 A1 | 10/2003 | Cully et al. |
| 2003/0195537 A1 | 10/2003 | Dubrul |
| 2003/0195554 A1 | 10/2003 | Shen |
| 2003/0199917 A1 | 10/2003 | Knudson |
| 2003/0204202 A1 | 10/2003 | Palmer |
| 2003/0212430 A1 | 11/2003 | Bose |
| 2003/0216611 A1 | 11/2003 | Q. Vu |
| 2003/0236533 A1 | 12/2003 | Wilson |
| 2004/0010280 A1 | 1/2004 | Adams et al. |
| 2004/0010282 A1 | 1/2004 | Kusleika |
| 2004/0014002 A1 | 1/2004 | Lundgren |
| 2004/0068288 A1 | 4/2004 | Palmer et al. |
| 2004/0073243 A1 | 4/2004 | Sepetka |
| 2004/0079429 A1 | 4/2004 | Miller |
| 2004/0082962 A1 | 4/2004 | Demarais et al. |
| 2004/0093065 A1 | 5/2004 | Yachia et al. |
| 2004/0133231 A1 | 7/2004 | Maitland |
| 2004/0138692 A1 | 7/2004 | Phung |
| 2004/0153049 A1 | 8/2004 | Hewitt et al. |
| 2004/0153118 A1 | 8/2004 | Clubb |
| 2004/0193107 A1 | 9/2004 | Pierpont et al. |
| 2004/0199202 A1 | 10/2004 | Dubrul et al. |
| 2004/0260333 A1 | 12/2004 | Dubrul et al. |
| 2005/0015047 A1 | 1/2005 | Shah |
| 2005/0020974 A1 | 1/2005 | Noriega |
| 2005/0033348 A1 | 2/2005 | Sepetka |
| 2005/0038447 A1 | 2/2005 | Huffmaster |
| 2005/0038468 A1 | 2/2005 | Panetta et al. |
| 2005/0049619 A1 | 3/2005 | Sepetka |
| 2005/0049669 A1 | 3/2005 | Jones |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0059993 A1* | 3/2005 | Ramzipoor ....... A61M 25/0069 606/200 |
| 2005/0059995 A1 | 3/2005 | Sepetka |
| 2005/0085849 A1 | 4/2005 | Sepetka |
| 2005/0090857 A1 | 4/2005 | Kusleika et al. |
| 2005/0119668 A1 | 6/2005 | Teague et al. |
| 2005/0125024 A1 | 6/2005 | Sepetka |
| 2005/0131449 A1 | 6/2005 | Salahieh et al. |
| 2005/0149111 A1 | 7/2005 | Kanazawa et al. |
| 2005/0171566 A1 | 8/2005 | Kanamaru |
| 2005/0187570 A1 | 8/2005 | Nguyen et al. |
| 2005/0267491 A1 | 8/2005 | Kellett et al. |
| 2005/0216030 A1 | 9/2005 | Sepetka |
| 2005/0216050 A1 | 9/2005 | Sepetka |
| 2005/0288686 A1 | 9/2005 | Sepetka |
| 2005/0228417 A1 | 10/2005 | Teitelbaum et al. |
| 2006/0009785 A1 | 1/2006 | Maitland et al. |
| 2006/0009799 A1 | 1/2006 | Kleshinski et al. |
| 2006/0010636 A1 | 1/2006 | Vacher |
| 2006/0030933 A1 | 2/2006 | DeLeggge et al. |
| 2006/0036271 A1 | 2/2006 | Schomer et al. |

(56) References Cited

U.S. PATENT DOCUMENTS

| | | |
|---|---|---|
| 2006/0058836 A1 | 3/2006 | Bose |
| 2006/0058837 A1 | 3/2006 | Bose |
| 2006/0058838 A1 | 3/2006 | Bose |
| 2006/0064151 A1 | 3/2006 | Guterman et al. |
| 2006/0149313 A1 | 7/2006 | Arguello et al. |
| 2006/0155305 A1 | 7/2006 | Freudenthal |
| 2006/0155322 A1 | 7/2006 | Sater et al. |
| 2006/0161187 A1 | 7/2006 | Levine et al. |
| 2006/0195137 A1 | 8/2006 | Sepetka |
| 2006/0224177 A1 | 10/2006 | Finitsis |
| 2006/0224179 A1 | 10/2006 | Kucharczyk |
| 2006/0229638 A1 | 10/2006 | Abrams et al. |
| 2006/0282111 A1 | 12/2006 | Morsi |
| 2006/0287701 A1 | 12/2006 | Pal |
| 2007/0088383 A1 | 4/2007 | Pal et al. |
| 2007/0142858 A1 | 6/2007 | Bates |
| 2007/0149996 A1 | 6/2007 | Coughlin |
| 2007/0156170 A1 | 7/2007 | Hancock |
| 2007/0165170 A1 | 7/2007 | Fukuda |
| 2007/0191866 A1 | 8/2007 | Palmer et al. |
| 2007/0198028 A1 | 8/2007 | Miloslavski |
| 2007/0198051 A1 | 8/2007 | Clubb et al. |
| 2007/0198075 A1 | 8/2007 | Levy |
| 2007/0208367 A1 | 9/2007 | Fiorella |
| 2007/0208371 A1 | 9/2007 | French |
| 2007/0213765 A1 | 9/2007 | Adams et al. |
| 2007/0225749 A1 | 9/2007 | Martin |
| 2007/0239254 A1 | 10/2007 | Chia et al. |
| 2007/0244505 A1 | 10/2007 | Gilson et al. |
| 2007/0270902 A1 | 11/2007 | Slazas et al. |
| 2007/0288038 A1 | 12/2007 | Bimbo |
| 2007/0293887 A1 | 12/2007 | Okushi et al. |
| 2008/0045881 A1 | 2/2008 | Teitelbaum et al. |
| 2008/0082107 A1 | 4/2008 | Miller et al. |
| 2008/0086190 A1 | 4/2008 | Ta |
| 2008/0091223 A1 | 4/2008 | Pokorney |
| 2008/0097398 A1 | 4/2008 | Mitelberg |
| 2008/0109031 A1 | 5/2008 | Sepetka |
| 2008/0109032 A1 | 5/2008 | Sepetka |
| 2008/0119886 A1 | 5/2008 | Greenhalgh et al. |
| 2008/0177296 A1 | 7/2008 | Sepetka |
| 2008/0183197 A1 | 7/2008 | Sepetka |
| 2008/0183198 A1 | 7/2008 | Sepetka |
| 2008/0183205 A1 | 7/2008 | Sepetka |
| 2008/0188876 A1 | 8/2008 | Sepetka |
| 2008/0188885 A1 | 8/2008 | Sepetka |
| 2008/0188928 A1 | 8/2008 | Salahieh |
| 2008/0200946 A1 | 8/2008 | Braun |
| 2008/0215077 A1 | 9/2008 | Sepetka |
| 2008/0221600 A1 | 9/2008 | Dieck et al. |
| 2008/0228209 A1 | 9/2008 | DeMello et al. |
| 2008/0234706 A1 | 9/2008 | Sepetka |
| 2008/0243170 A1 | 10/2008 | Jenson |
| 2008/0255596 A1 | 10/2008 | Jenson |
| 2008/0262528 A1 | 10/2008 | Martin |
| 2008/0262532 A1 | 10/2008 | Martin |
| 2008/0275488 A1 | 11/2008 | Fleming |
| 2008/0275493 A1 | 11/2008 | Farmiga |
| 2008/0281350 A1 | 11/2008 | Sepetka |
| 2008/0312681 A1 | 12/2008 | Ansel |
| 2009/0024157 A1 | 1/2009 | Anukhin |
| 2009/0054918 A1 | 2/2009 | Henson |
| 2009/0069828 A1 | 3/2009 | Martin |
| 2009/0076539 A1 | 3/2009 | Valaie |
| 2009/0105722 A1 | 4/2009 | Fulkerson |
| 2009/0105737 A1 | 4/2009 | Fulkerson |
| 2009/0131908 A1 | 5/2009 | McKay |
| 2009/0163846 A1 | 5/2009 | Aklog et al. |
| 2009/0177206 A1 | 7/2009 | Lozier et al. |
| 2009/0182336 A1 | 7/2009 | Brenzel et al. |
| 2009/0221967 A1 | 9/2009 | Thommen et al. |
| 2009/0270815 A1 | 10/2009 | Stamp et al. |
| 2009/0281610 A1 | 11/2009 | Parker |
| 2009/0292297 A1 | 11/2009 | Ferrere |
| 2009/0292307 A1 | 11/2009 | Razack |
| 2009/0299374 A1 | 12/2009 | Tilson et al. |
| 2009/0299393 A1 | 12/2009 | Martin |
| 2009/0306702 A1 | 12/2009 | Miloslavski |
| 2010/0004607 A1 | 1/2010 | Wilson et al. |
| 2010/0016957 A1 | 1/2010 | Jager et al. |
| 2010/0030186 A1 | 2/2010 | Stivland |
| 2010/0030256 A1 | 2/2010 | Dubrul et al. |
| 2010/0036312 A1 | 2/2010 | Krolik et al. |
| 2010/0087908 A1 | 4/2010 | Hilaire |
| 2010/0114017 A1 | 5/2010 | Lenker |
| 2010/0125326 A1 | 5/2010 | Kalstad |
| 2010/0125327 A1 | 5/2010 | Agnew |
| 2010/0191272 A1 | 7/2010 | Keating |
| 2010/0211094 A1 | 8/2010 | Sargent, Jr. |
| 2010/0249815 A1 | 9/2010 | Jantzen et al. |
| 2010/0268264 A1 | 10/2010 | Bonnett et al. |
| 2010/0268265 A1 | 10/2010 | Krolik et al. |
| 2010/0292726 A1 | 11/2010 | Olsen et al. |
| 2010/0305566 A1 | 12/2010 | Rosenblatt et al. |
| 2010/0305604 A1 | 12/2010 | Pah |
| 2010/0318178 A1 | 12/2010 | Rapaport et al. |
| 2010/0324649 A1 | 12/2010 | Mattsson |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0009942 A1 | 1/2011 | Gregorich |
| 2011/0022149 A1 | 1/2011 | Cox et al. |
| 2011/0054514 A1 | 3/2011 | Arcand |
| 2011/0054516 A1 | 3/2011 | Keegan |
| 2011/0060359 A1 | 3/2011 | Hannes |
| 2011/0071432 A1 | 3/2011 | Carrillo, Jr. et al. |
| 2011/0077620 A1 | 3/2011 | deBeer |
| 2011/0098683 A1 | 4/2011 | Wiita et al. |
| 2011/0054504 A1 | 5/2011 | Wolf et al. |
| 2011/0125181 A1 | 5/2011 | Brady et al. |
| 2011/0130756 A1 | 6/2011 | Everson, Jr. et al. |
| 2011/0152920 A1 | 6/2011 | Eckhouse et al. |
| 2011/0160763 A1 | 6/2011 | Ferrera et al. |
| 2011/0166586 A1 | 7/2011 | Sepetka et al. |
| 2011/0196414 A1 | 8/2011 | Porter et al. |
| 2011/0202088 A1 | 8/2011 | Eckhouse et al. |
| 2011/0213290 A1 | 9/2011 | Chin et al. |
| 2011/0213297 A1 | 9/2011 | Aklog et al. |
| 2011/0213393 A1 | 9/2011 | Aklog et al. |
| 2011/0213403 A1 | 9/2011 | Aboytes |
| 2011/0218564 A1 | 9/2011 | Drasler et al. |
| 2011/0224707 A1 | 9/2011 | Miloslavski et al. |
| 2011/0264132 A1 | 10/2011 | Strauss et al. |
| 2011/0276120 A1 | 11/2011 | Gilson et al. |
| 2011/0319917 A1 | 12/2011 | Ferrera et al. |
| 2012/0041449 A1 | 2/2012 | Eckhouse et al. |
| 2012/0041474 A1 | 2/2012 | Eckhouse et al. |
| 2012/0059356 A1 | 3/2012 | diPama et al. |
| 2012/0089216 A1 | 4/2012 | Rapaport et al. |
| 2012/0101510 A1 | 4/2012 | Lenker et al. |
| 2012/0116351 A1 | 5/2012 | Chomas et al. |
| 2012/0116440 A1 | 5/2012 | Leynov et al. |
| 2012/0143237 A1 | 6/2012 | Cam et al. |
| 2012/0143239 A1 | 6/2012 | Aklog et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0215250 A1 | 8/2012 | Grandfield et al. |
| 2012/0277788 A1 | 11/2012 | Cattaneo |
| 2012/0283768 A1 | 11/2012 | Cox et al. |
| 2012/0296362 A1 | 11/2012 | Cam et al. |
| 2012/0316600 A1 | 12/2012 | Ferrera et al. |
| 2013/0006284 A1 | 1/2013 | Aggerholm et al. |
| 2013/0030461 A1 | 1/2013 | Marks et al. |
| 2013/0046330 A1 | 2/2013 | McIntosh et al. |
| 2013/0046333 A1 | 2/2013 | Jones et al. |
| 2013/0046334 A1 | 2/2013 | Jones et al. |
| 2013/0116774 A1 | 5/2013 | Strauss et al. |
| 2013/0131614 A1 | 5/2013 | Hassan et al. |
| 2013/0144326 A1 | 6/2013 | Brady et al. |
| 2013/0144328 A1 | 6/2013 | Weber et al. |
| 2013/0158592 A1 | 6/2013 | Porter |
| 2013/0184703 A1 | 7/2013 | Shireman et al. |
| 2013/0184739 A1 | 7/2013 | Brady et al. |

(56) References Cited

U.S. PATENT DOCUMENTS

| | | |
|---|---|---|
| 2013/0197567 A1 | 8/2013 | Brady et al. |
| 2013/0226146 A1 | 8/2013 | Tekulve |
| 2013/0268050 A1 | 10/2013 | Wilson et al. |
| 2013/0281788 A1 | 10/2013 | Garrison |
| 2013/0289697 A1 | 10/2013 | Baker et al. |
| 2013/0325055 A1 | 12/2013 | Eckhouse et al. |
| 2013/0325056 A1 | 12/2013 | Eckhouse et al. |
| 2013/0345739 A1 | 12/2013 | Brady et al. |
| 2014/0012281 A1 | 1/2014 | Wang et al. |
| 2014/0046359 A1 | 2/2014 | Bowman et al. |
| 2014/0052097 A1 | 2/2014 | Petersen et al. |
| 2014/0081243 A1 | 3/2014 | Zhou et al. |
| 2014/0121672 A1 | 5/2014 | Folk |
| 2014/0128905 A1 | 5/2014 | Molaei |
| 2014/0135812 A1 | 5/2014 | Divino et al. |
| 2014/0180377 A1 | 6/2014 | Bose et al. |
| 2014/0188127 A1 | 7/2014 | Dubrul et al. |
| 2014/0194919 A1 | 7/2014 | Losordo et al. |
| 2014/0200607 A1 | 7/2014 | Sepetka et al. |
| 2014/0200608 A1 | 7/2014 | Brady et al. |
| 2014/0236220 A1 | 8/2014 | Inoue |
| 2014/0257018 A1 | 9/2014 | Farnan |
| 2014/0257362 A1 | 9/2014 | Eldenschink |
| 2014/0276922 A1 | 9/2014 | McLain et al. |
| 2014/0277003 A1 | 9/2014 | Hendrick |
| 2014/0277053 A1 | 9/2014 | Wang et al. |
| 2014/0277079 A1 | 9/2014 | Vale et al. |
| 2014/0309657 A1 | 10/2014 | Ben-Ami |
| 2014/0309673 A1 | 10/2014 | Dacuycuy et al. |
| 2014/0330302 A1 | 11/2014 | Tekulve et al. |
| 2014/0343585 A1 | 11/2014 | Ferrera et al. |
| 2014/0364896 A1 | 12/2014 | Consigny |
| 2014/0371769 A1 | 12/2014 | Vale et al. |
| 2014/0371777 A1 | 12/2014 | Rudakov et al. |
| 2014/0371779 A1 | 12/2014 | Vale et al. |
| 2014/0371780 A1 | 12/2014 | Vale et al. |
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0080937 A1 | 3/2015 | Davidson |
| 2015/0081003 A1 | 3/2015 | Wainwright et al. |
| 2015/0112376 A1 | 4/2015 | Molaei et al. |
| 2015/0133990 A1 | 5/2015 | Davidson |
| 2015/0142043 A1 | 5/2015 | Furey |
| 2015/0164523 A1 | 6/2015 | Brady et al. |
| 2015/0173782 A1 | 6/2015 | Garrison et al. |
| 2015/0173783 A1 | 6/2015 | Tah et al. |
| 2015/0238314 A1 | 8/2015 | Börtlein et al. |
| 2015/0250497 A1 | 9/2015 | Marks et al. |
| 2015/0257775 A1 | 9/2015 | Gilvarry et al. |
| 2015/0258270 A1 | 9/2015 | Kunis |
| 2015/0290437 A1 | 10/2015 | Rudakov et al. |
| 2015/0297252 A1 | 10/2015 | Miloslavski et al. |
| 2015/0306311 A1 | 10/2015 | Pinchuk et al. |
| 2015/0313617 A1 | 11/2015 | Grandfield et al. |
| 2015/0320431 A1 | 11/2015 | Ulm, III |
| 2015/0351770 A1 | 12/2015 | Fulton, III |
| 2015/0352325 A1 | 12/2015 | Quick |
| 2015/0359547 A1 | 12/2015 | Vale et al. |
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022296 A1 | 1/2016 | Brady et al. |
| 2016/0066921 A1 | 3/2016 | Brady et al. |
| 2016/0074067 A1 | 3/2016 | Furnish et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0121080 A1 | 5/2016 | Cottone |
| 2016/0135829 A1 | 5/2016 | Holochwost et al. |
| 2016/0143653 A1 | 5/2016 | Vale et al. |
| 2016/0151079 A1 | 6/2016 | Aklog et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0228134 A1 | 8/2016 | Martin et al. |
| 2016/0256180 A1 | 9/2016 | Vale et al. |
| 2016/0262880 A1 | 9/2016 | Li et al. |
| 2016/0317168 A1 | 11/2016 | Brady et al. |
| 2016/0346002 A1 | 12/2016 | Avneri et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0065401 A1 | 3/2017 | Fearnot et al. |
| 2017/0071614 A1 | 3/2017 | Vale et al. |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086862 A1 | 3/2017 | Vale et al. |
| 2017/0086863 A1 | 3/2017 | Brady et al. |
| 2017/0086864 A1 | 3/2017 | Greenhalgh et al. |
| 2017/0086996 A1 | 3/2017 | Peterson et al. |
| 2017/0239447 A1 | 3/2017 | Greenhalgh et al. |
| 2017/0095138 A1 | 4/2017 | Nakade et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0105743 A1 | 4/2017 | Vale et al. |
| 2017/0112515 A1 | 4/2017 | Brady et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172554 A1 | 6/2017 | Bortlein et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0238953 A1 | 8/2017 | Yang et al. |
| 2017/0252043 A1 | 9/2017 | Fuller et al. |
| 2017/0252064 A1 | 9/2017 | Staunton |
| 2017/0259042 A1 | 9/2017 | Nguyen et al. |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Sethna |
| 2017/0290654 A1 | 10/2017 | Sethna |

(56) References Cited

U.S. PATENT DOCUMENTS

| | | |
|---|---|---|
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0008407 A1 | 1/2018 | Maimon et al. |
| 2018/0042623 A1 | 2/2018 | Batiste |
| 2018/0193050 A1 | 7/2018 | Hawkins et al. |
| 2018/0193591 A1 | 7/2018 | Jaroch et al. |
| 2018/0235743 A1 | 8/2018 | Farago et al. |
| 2018/0256177 A1 | 9/2018 | Cooper et al. |
| 2018/0303610 A1 | 10/2018 | Anderson |
| 2019/0021755 A1 | 1/2019 | Johnson et al. |
| 2019/0021759 A1 | 1/2019 | Krolik et al. |
| 2019/0029820 A1 | 1/2019 | Zhou et al. |
| 2019/0029825 A1 | 1/2019 | Fitterer et al. |
| 2019/0046219 A1 | 2/2019 | Marchand et al. |
| 2019/0192175 A1 | 6/2019 | Chida et al. |
| 2019/0209206 A1 | 7/2019 | Patel et al. |
| 2019/0216476 A1 | 7/2019 | Barry et al. |
| 2019/0239907 A1 | 8/2019 | Brady et al. |
| 2019/0247627 A1 | 8/2019 | Korkuch et al. |
| 2019/0255290 A1 | 8/2019 | Snyder et al. |
| 2019/0269491 A1 | 9/2019 | Jalgaonkar et al. |
| 2019/0274810 A1 | 9/2019 | Phouasalit et al. |
| 2019/0298396 A1 | 10/2019 | Gamba et al. |
| 2019/0365411 A1 | 12/2019 | Avneri et al. |
| 2019/0366049 A1 | 12/2019 | Hannon et al. |
| 2020/0038628 A1 | 2/2020 | Chou et al. |
| 2020/0214859 A1 | 7/2020 | Sherburne |
| 2020/0281611 A1 | 9/2020 | Kelly et al. |
| 2020/0353208 A1 | 11/2020 | Merhi et al. |
| 2020/0383698 A1 | 12/2020 | Miao et al. |
| 2021/0085935 A1 | 3/2021 | Fahey et al. |
| 2021/0153883 A1 | 5/2021 | Casey et al. |
| 2021/0153884 A1 | 5/2021 | Casey et al. |
| 2021/0154433 A1 | 5/2021 | Casey et al. |
| 2021/0219821 A1 | 7/2021 | Appling et al. |
| 2022/0117614 A1 | 4/2022 | Salmon et al. |
| 2022/0125450 A1 | 4/2022 | Sirhan et al. |
| 2022/0313426 A1 | 10/2022 | Gifford et al. |
| 2023/0054898 A1 | 3/2023 | Gurovich et al. |

FOREIGN PATENT DOCUMENTS

| | | |
|---|---|---|
| CN | 103071195 A | 5/2013 |
| CN | 104507380 A | 4/2015 |
| CN | 104905873 A | 9/2015 |
| CN | 105007973 A | 10/2015 |
| CN | 105307582 A | 2/2016 |
| CN | 105726163 A | 7/2016 |
| CN | 106232059 A | 12/2016 |
| CN | 113040865 A | 6/2021 |
| DE | 20 2009 001 951 U1 | 4/2010 |
| DE | 10 2009 056 450 A1 | 6/2011 |
| DE | 10 2010 010 849 A1 | 9/2011 |
| DE | 10 2010 014 778 A1 | 10/2011 |
| DE | 10 2010 024 085 A1 | 12/2011 |
| DE | 10 2011 014 586 B3 | 9/2012 |
| DE | 20 2020 107013 U1 | 1/2021 |
| EP | 2301450 A1 | 3/2011 |
| EP | 2628455 A1 | 8/2013 |
| EP | 3302312 A1 | 4/2018 |
| EP | 3335647 A2 | 6/2018 |
| EP | 3 420 978 A1 | 1/2019 |
| EP | 4049704 A2 | 8/2022 |
| GB | 2498349 A | 7/2013 |
| JP | 9-19438 A | 1/1997 |
| WO | WO 93/04722 A2 | 3/1993 |
| WO | 94/24926 A1 | 11/1994 |
| WO | 97/27808 A1 | 8/1997 |
| WO | 97/38631 A1 | 10/1997 |
| WO | 99/20335 A1 | 4/1999 |
| WO | 99/56801 A2 | 11/1999 |
| WO | 99/60933 A1 | 12/1999 |
| WO | 01/21077 A1 | 3/2001 |
| WO | 02/02162 A2 | 1/2002 |
| WO | 02/11627 A2 | 2/2002 |
| WO | 02/43616 A2 | 6/2002 |
| WO | 02/070061 A1 | 9/2002 |
| WO | 02/094111 A2 | 11/2002 |
| WO | 03/002006 A1 | 1/2003 |
| WO | 03/018085 A2 | 3/2003 |
| WO | 03/030751 A1 | 4/2003 |
| WO | 03/051448 A2 | 6/2003 |
| WO | 2004/028571 A1 | 4/2004 |
| WO | 2004/056275 A1 | 7/2004 |
| WO | 2005/000130 A1 | 1/2005 |
| WO | 2005/027779 A2 | 3/2005 |
| WO | WO 2005/027751 A1 | 3/2005 |
| WO | 2006/021407 A2 | 3/2006 |
| WO | 2006/031410 A2 | 3/2006 |
| WO | 2006/107641 A2 | 10/2006 |
| WO | 2006/135823 A2 | 12/2006 |
| WO | 2007/054307 A2 | 5/2007 |
| WO | 2007/068424 A2 | 6/2007 |
| WO | 2008/034615 A2 | 3/2008 |
| WO | 2008/051431 A1 | 5/2008 |
| WO | 2008/131116 A1 | 10/2008 |
| WO | WO 2009/019664 A1 | 2/2009 |
| WO | 2009/031338 A1 | 3/2009 |
| WO | 2009/076482 A1 | 6/2009 |
| WO | 2009/086482 A2 | 7/2009 |
| WO | 2009/105710 A1 | 8/2009 |
| WO | WO 2009/103125 A1 | 8/2009 |
| WO | 2010/010545 A1 | 1/2010 |
| WO | 2010/046897 A1 | 4/2010 |
| WO | 2010/075565 A1 | 7/2010 |
| WO | 2010/102307 A1 | 9/2010 |
| WO | 2010/146581 A1 | 12/2010 |
| WO | 2011/013556 A1 | 2/2011 |
| WO | 2011/066961 A1 | 6/2011 |
| WO | 2011/082319 A1 | 7/2011 |
| WO | 2011/095352 A1 | 8/2011 |
| WO | 2011/106426 A1 | 9/2011 |
| WO | 2011/110316 A1 | 9/2011 |
| WO | 2012/052982 A1 | 4/2012 |
| WO | 2012/064726 A1 | 5/2012 |
| WO | 2012/081020 A1 | 6/2012 |
| WO | 2012/110619 A1 | 8/2012 |
| WO | 2012/120490 A2 | 9/2012 |
| WO | 2012/156924 A1 | 11/2012 |
| WO | 2013/016435 A1 | 1/2013 |
| WO | 2013/072777 A2 | 5/2013 |
| WO | 2013/105099 A2 | 7/2013 |
| WO | 2013/109756 A2 | 7/2013 |
| WO | 2014/081892 A1 | 5/2014 |
| WO | 2014/139845 A1 | 9/2014 |
| WO | 2014/169266 A1 | 10/2014 |
| WO | 2014/178198 A1 | 11/2014 |
| WO | WO 2014/188300 A1 | 11/2014 |
| WO | 2015/061365 A1 | 4/2015 |
| WO | 2015/134625 A1 | 9/2015 |
| WO | 2015/179324 A2 | 11/2015 |
| WO | WO 2015/179377 A1 | 11/2015 |
| WO | 2015/189354 A1 | 12/2015 |
| WO | 2016/010995 A1 | 1/2016 |
| WO | WO 2017/004234 A1 | 1/2017 |
| WO | WO 2017/097616 A1 | 6/2017 |
| WO | 2018/193603 A1 | 10/2018 |

(56) References Cited

FOREIGN PATENT DOCUMENTS

| WO | WO 2018/178979 A1 | 10/2018 |
| WO | WO 2019/064306 A1 | 4/2019 |
| WO | WO 2019/079296 A1 | 4/2019 |
| WO | WO 2020/139979 A1 | 7/2020 |
| WO | WO 2021/016213 A1 | 1/2021 |
| WO | WO 2021/167653 A1 | 8/2021 |
| WO | WO 2022/020366 A2 | 1/2022 |

OTHER PUBLICATIONS

Extended European Search Report issued in corresponding European Patent Application No. 20 20 9993 dated Apr. 1, 2021.
Struffert, T., et al. "Intravenous flat detector CT angiography for non-invasive visualisation of intracranial flow diverter: technical feasibility" Eur Radiol 21:1797-1801 (2011).

* cited by examiner

CLOT RETRIEVAL DEVICE WITH OUTER SHEATH AND INNER CATHETER

CROSS-REFERENCE TO RELATED APPLICATION

The present application claims the benefit of priority of U.S. Provisional Patent Application No. 62/941,366, filed on Nov. 27, 2019 and incorporated herein by reference in its entirety.

FIELD OF THE INVENTION

The present invention generally relates to devices and methods for removing blockages from blood vessels during intravascular medical treatments. More specifically, the present invention relates to a clot retrieval device comprising an outer sheath and an inner funnel catheter.

BACKGROUND

Clot retrieval catheters and devices are used in mechanical thrombectomy for endovascular intervention, often in cases where patients are suffering from conditions such as acute ischemic stroke (AIS), myocardial infarction (MI), and pulmonary embolism (PE). Accessing the neurovascular bed in particular is challenging with conventional technology, as the target vessels are small in diameter, remote relative to the site of insertion, and are highly tortuous. Traditional devices are often either too large in profile, lack the deliverability and flexibility needed to navigate tortuous vessels, difficult to administer and use, or are not effective at removing a clot when delivered to the target site.

The delivery of effective devices to the small and highly-branched cerebral artery system remains challenging, and conventional clot retrieval catheters suffer from a number of drawbacks. First, the diameters of catheters themselves must be small enough to avoid causing significant discomfort to the patient. The retrieval catheter must also be sufficiently flexible to navigate the vasculature and endure high strains, while also having the axial stiffness to offer smooth advancement along the route. Once at the target site, typical objects to be retrieved from the body are substantially larger in size than the catheter tip, making it more difficult to retrieve objects into the tip. For example, firm, fibrin-rich clots can often be difficult to extract as they can become lodged in the tip of traditional fixed-mouth catheters. Additionally, this lodging can cause softer portions to shear away from the firmer regions of the clot.

Small diameters and fixed tip sizes are also less efficient at directing the aspiration necessary to remove blood and thrombus material during the procedure. The suction must be strong enough such that any fragmentation that may occur as a result of aspiration or the use of a mechanical thrombectomy device cannot migrate and occlude distal vessels. However, when aspirating with a fixed-mouth catheter, a significant portion of the aspiration flow ends up coming from vessel fluid proximal to the tip of the catheter, where there is no clot. This significantly reduces aspiration efficiency, lowering the success rate of clot removal.

Any catheter design attempting to overcome these challenges with an expanding distal tip or structure would need to have the strength to grip the clot and exert a steady radial force in the expanded state. The same structure would also need to be sufficiently flexible and elastic to survive the severe mechanical strains imparted when navigating the tortuous vasculature when in a collapsed state.

Further, other catheter designs can present challenges to operators in requiring the management and relative positioning of separate, catheters or other components without mechanisms to stabilize their positioning relative to one another or aid in deliverability of the components in an atraumatic manner. This can lead to traumatic or inaccurate deployment of the catheter and/or devices at the target site.

The present design is aimed at providing an improved retrieval catheter which addresses the above-stated deficiencies.

SUMMARY

It is an object of the present design to provide devices and methods to meet the above-stated needs. It is therefore desirable for a clot retrieval catheter device to have a large-mouth expandable tip for removal and easy retrieval of the clot while also having a collapsed state that is low-profile and sufficiently flexible for deliverability to the target site. The device should also incorporate treatment administration enhancements over existing designs to assist administrators in operating the device. According to the present invention, there is provided a device which can have an outer sheath facilitating the introduction of microcatheters, guidewires, or any of a number of commercially available products to a target site within the vasculature. The outer sheath can be one or both of a guide catheter and an intermediate catheter. The outer sheath can have a distal end, a proximal end, a proximal luer containing the proximal end, and an internal lumen extending proximal of the distal end and terminating within the proximal luer. In some examples, at least a portion of the distal end can be encompassed by a flexible membrane.

Within the outer sheath can be an inner funnel catheter having an expandable distal tip. The expandable distal tip can have a supporting structure comprised of struts or a braided mesh. The inner funnel catheter may be pre-loaded into the outer sheath prior to the administration of the device to a target site.

The inner funnel catheter can have a proximal end, a distal end, a proximal luer containing the proximal end, and an internal lumen extending proximal of the distal end and terminating within the luer. The inner funnel catheter can also have a rapid exchange shaft or guidewire extending proximal to the luer.

The inner funnel catheter tip may be self-expanding and disposed at the distal end of the inner funnel catheter. The tip can have a collapsed delivery configuration and a radially expanded deployed configuration in which the tip assumes a substantially conical or funnel shape. The distal tip can be configured to radially self-expand when unconstrained distal of the distal end of the outer sheath. In the collapsed state, the tip can have a radial dimension less than a maximum radial dimension of the tip. When expanded, the tip can grow radially outward to form an open distal mouth. In some examples, at least a portion of the tip can assume a diameter greater than the diameter of the outer sheath. In the expanded state, the tip can contact, and form a seal with, the inner wall of a blood vessel.

The large distal mouth can offer improved performance over conventional fixed-mouth designs. Traditional fixed-mouth catheters can be hindered by having firm, fibrin-rich clots lodge in the tip, or by having softer portions of the clot shear away. In addition, when aspirating through a fixed-mouth catheter, a significant portion of the suction is directed to fluid proximal of the tip, reducing the suction directed to the clot. In addition, as the diameter of an expandable tip can be close to that of the vessel, clot shearing at the mouth of the catheter can be mitigated and the volume of fluid and clot distal of the tip secured.

At least a portion of the tip of the inner funnel catheter can have a membrane disposed around it. In some examples, a membrane can cover both the tip and some or all of the outer sheath. For example, a membrane can be attached to the distal end of the outer sheath and expanded radially by the radial self-expansion of the distal tip. In another example, a membrane can be attached to both the inner diameter of the inner funnel catheter and the outer diameter of the outer sheath so that it is expanded radially by the radial self-expansion of the distal tip.

The tip can be constructed from a sheet or tube stainless steel, or a superelastic shape memory alloy such as Nitinol. In another example, the tip can have a braided construction from wire or strip. In a further example, the tip can be a lattice laser cut from a hypotube. The shape radial dimensions of the tip can be designed to atraumatically contact the circumference of the inner wall of a blood vessel.

In an example, the distal end of the outer sheath can be delivered approximate a target site. The proximal luer of the outer sheath can be kept in a fixed position so as to maintain the positioning of the distal end of the outer sheath relative to the target site. The inner funnel catheter can be present inside the lumen of the outer sheath. The proximal luer of the inner funnel catheter can be moved distally towards the proximal luer of the outer sheath to advance the distal end of the inner funnel catheter towards the target site. The proximal luer of the inner funnel catheter can also be moved proximally away from the proximal luer of the outer sheath to retract the inner funnel catheter away from the target site.

In some examples, the proximal luer of the inner funnel catheter can connect axially to the proximal luer of the outer sheath. When connected, the proximal luer of the outer sheath can be located distally to the proximal luer of the funnel catheter. The connection between the luers may be accomplished via snap fit features, luer lock threads, a locking tab, or other suitable joining mechanisms.

The proximal luer of the funnel catheter can contain a mechanism for changing the longitudinal position of the inner funnel catheter relative to the outer sheath. In one examples, the proximal luer of the funnel catheter can contain a slider mechanism for moving the inner funnel catheter telescopically relative to a fixed position of the outer sheath. By moving the slider mechanism distally across the funnel catheter's proximal luer, the funnel catheter can be deployed to extend past the distal end of the outer sheath.

Alternatively, the proximal luer of the outer sheath can have a slider mechanism for moving the outer sheath telescopically relative to a fixed position of the inner funnel catheter. Retracting the slider mechanism can retract the outer sheath body relative to the funnel catheter, allowing the expandable tip of the funnel catheter to be exposed and deployed in situ. In one example, the slider mechanism can deploy the inner funnel catheter by using a pulley pull wire set in the funnel catheter luer. Additionally, the slider can be advanced distally across the outer sheath's proximal luer to re-advance the outer sheath to encompass the distal end of the funnel catheter and return the configuration of the expandable tip of the funnel catheter to the collapsed state.

In some examples, the inner funnel catheter may be withdrawn from inside the outer sheath by fixing the position of the proximal luer of the outer sheath and retracting the proximal luer of the funnel catheter to extract the inner funnel catheter. A loading tool may be supplied to aid in re-advancing the funnel catheter through the outer sheath if the funnel catheter is replaced after removal. The loading tool can incorporate a split or semi-split design so that it can be peeled on or off the inner funnel catheter.

In another example, the slider mechanism in the outer sheath's proximal luer can be retracted to retract the outer sheath relative to the inner funnel catheter. When the outer sheath is retracted, the expandable tip can be uncovered to expand and deploy just proximate the target site.

The distal tip can have a collapsed delivery position axially within the outer sheath during advancement to the obstruction in the blood vessel. In some examples, the distance between the distal end of the outer sheath and the distal end of the inner funnel catheter in the collapsed delivery position inside the outer sheath can be close to zero so that minimal movement is required to deploy the inner funnel catheter. In another example, the distance between the distal end of the outer sheath and the distal end of the inner funnel catheter can range between 1 to 100 mm to facilitate the distal flexibility of the outer sheath. In a more specific example, the collapsed delivery position of the distal tip is a distance between approximately 20-50 mm proximal of the distal end of the outer sheath.

In another example, the mechanism for advancing or retracting the position of the outer sheath relative to the inner funnel catheter can be a rotating knob. Angular rotation of the knob can be translated into linear motion of the outer sheath. By rotating the knob in a counterclockwise or clockwise direction, the position of the outer sheath may be advanced distally or retracted proximally relative to the position of the inner funnel catheter.

In some examples, the inner funnel catheter luer can contain a port for connecting a syringe. Channels can be provided between the outer sheath luer and the funnel catheter luer so that both the inner funnel catheter and the outer sheath may be flushed simultaneously via fluid injected from a syringe connected to the port of the inner funnel catheter.

In another example, a locking tab can connect the proximal luer of the inner funnel catheter to the proximal luer of the outer sheath. The locking tab can hold the outer sheath and inner funnel catheter together for advancement. The locking tab can be removed before deploying the funnel catheter, as the distance between the distal end of the outer catheter and the collapsed funnel during advancement has been maintained. After the locking tab has been removed, the proximal luer of the inner funnel catheter and the proximal luer of the outer sheath can connect via a connection mechanism. This connection mechanism can include snap fit features, luer lock threads, or other joining mechanisms. The proximal luer of the inner funnel catheter and the proximal luer of the outer sheath can later be disconnected and the proximal luer of the outer sheath moved distally away from the proximal luer of the inner funnel catheter to recover the inner funnel catheter within the outer sheath.

Also provided is a method for removing an occlusive obstruction from a blood vessel. The method can have some or all of the following steps and variations thereof, and the steps are recited in no particular order. The method can have the steps advancing an outer sheath comprising a distal end, a proximal end, and a proximal luer containing the proximal end into the vasculature; advancing an inner funnel catheter telescopically moveable within the outer sheath and comprising a proximal end, a distal end, and a proximal luer containing the proximal end through the outer sheath until an expandable distal tip of the inner funnel catheter extends distal of the distal end of the outer sheath and deploys adjacent to an obstructive thrombus; capturing the thrombus in the mouth of the inner funnel catheter; and retrieving the inner funnel catheter with the captured thrombus through the vasculature and out of the patient.

When delivered to the target site, the expandable tip of the inner funnel catheter can be deployed to self-expand radially in order to contact the inner walls of the blood vessel. The profile of the tip can atraumatically seal against the vessel wall proximal of the target site. This can block vessel fluid proximal to the mouth and provides a large opening to easily receive the clot. For this reason, the method may further include the step of coating the expandable distal tip with a membrane. Alternatively, this step could involve advancing the distal tip distally to expand a membrane attached to the distal end of the outer sheath, or a membrane connected to both the funnel catheter and the outer sheath.

In an example, the step of advancing an inner funnel catheter through the outer sheath can comprise moving the proximal luer of the inner funnel catheter distally towards the proximal luer of the outer sheath to advance the distal end of the inner funnel catheter towards a target site. Alternately, a locking mechanism can be used to hold the inner funnel catheter and outer sheath together for distal advancement. In some examples, the locking mechanism can be one of a locking tab, snap fit feature, or luer lock thread.

Moving the inner funnel catheter and the outer sheath telescopically relative to each other can be accomplished by utilizing a sliding mechanism or rotating knob. In one example, the proximal luer of the inner funnel catheter can have a slider mechanism for advancing or retracting the position of the funnel catheter relative to the outer sheath, and the method can further contain the step of moving the slider mechanism distally across the funnel catheter's proximal luer to deploy the distal end of the funnel catheter to extend past the distal end of the outer sheath.

In another example, the proximal luer of the outer sheath can have a slider mechanism for advancing or retracting the position of the outer sheath relative to the funnel mechanism, and the method can further include the step of retracting the slider mechanism proximally to expose and thereby deploy the tip of the inner funnel catheter past the distal end of the outer sheath.

In a further example, the proximal luer of the outer sheath can have a rotating knob for advancing and retracting the position of the outer sheath relative to the inner funnel catheter, and the method can further include the step of rotating the knob to retract the outer sheath proximally relative to the inner funnel catheter.

The step of capturing the thrombus into the mouth of the clot retrieval catheter can comprise using aspiration, thrombectomy devices, or other practices and medical devices known in the art.

In many cases, after retrieving some or all of the occlusive clot, contrast media can be injected to allow a more thorough assessment of the degree to which the vessel is patent. Additional passes with the inner funnel catheter and/or clot retrieval device can be made if an obstruction remains in the vessel. The method can thus also have the step of maintaining the position of the outer sheath at the target site while the inner funnel catheter is retrieved. This can ensure access to the target site is not lost for subsequent retrieval attempts. Any remaining devices can then be removed from the patient once adequate recanalization of the target vessel is observed.

To clean the outer sheath and inner funnel catheter between passes or at the conclusion of the procedure, the method can further have the step of flushing simultaneously both the outer sheath and inner funnel catheter to remove lodged or loose debris. A plurality of channels can be formed between the proximal luer of the outer sheath and the proximal luer of the inner funnel catheter to allow both to be flushed simultaneously.

Other aspects and features of the present disclosure will become apparent to those of ordinary skill in the art, upon reviewing the following detailed description in conjunction with the accompanying figures.

BRIEF DESCRIPTION OF THE DRAWINGS

The above and further aspects of this invention are further discussed with the following description of the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation. It is expected that those of skill in the art can conceive of and combine elements from multiple figures to better suit the needs of the user.

DETAILED DESCRIPTION

Specific examples of the present invention are now described in detail with reference to the Figures, where identical reference numbers indicate elements which are functionally similar or identical.

Accessing the various vessels within the vascular, whether they are coronary, pulmonary, or cerebral, involves well-known procedural steps and the use of a number of conventional, commercially available accessory products.

These products, such as angiographic materials, rotating hemostasis valves, and guidewires are widely used in laboratory and medical procedures. When these products are employed in conjunction with the system and methods of this invention in the description below, their function and exact constitution are not described in detail.

Figure 1:
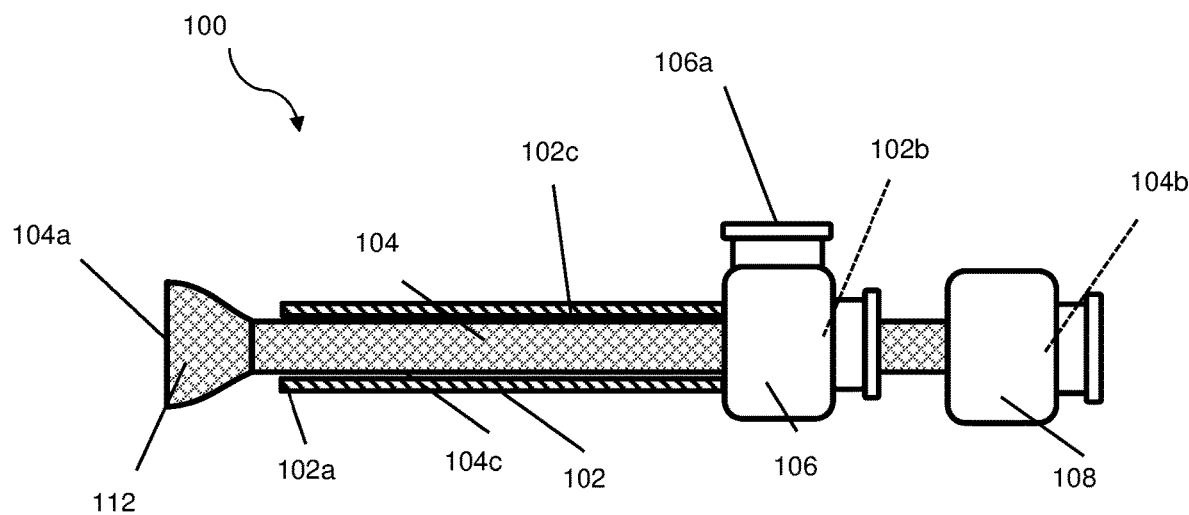
FIG. 1 is an illustration of a device having an outer sheath and an inner funnel catheter with the inner funnel catheter deployed according to aspects of the present invention.

Referring to the figures, in FIG. 1 there is illustrated a device 100 for removing an occlusive clot from a vessel of a patient according to this invention. The device 100 can have an outer sheath 102 facilitating the introduction of microcatheters, guidewires, or any of a number of commercially available products to a target site within the vasculature. The outer sheath 102 can be one or both of a guide catheter and an intermediate catheter. The outer sheath 102 can have a distal end 102a, a proximal end 102b, a proximal luer 106 containing the proximal end 102b, and an internal lumen 102c extending proximal of the distal end 102a and terminating within the proximal luer 106. In addition to introducing other devices, the lumen can direct aspiration from the proximal end 102a to the distal end 102b of the outer sheath 102. The outer sheath 102 can be positioned within the vasculature of a patient so that the distal end 102a is proximate a target occlusive clot.

The system 100 can also have an inner funnel catheter 104 with an expanding distal tip 112. The inner funnel catheter 104 can be located within the outer sheath 102. In some examples, the inner funnel catheter is concentric with and configured to move telescopically within the outer sheath 102. The inner funnel catheter 104 may be pre-loaded into the outer sheath 102 prior to the administration of the device 100 to a target site. Alternatively, the inner funnel catheter 104 may be inserted into the outer sheath 102 after the outer sheath 102 is positioned within the vasculature of a patient.

The inner funnel catheter may have a proximal end 104b, a distal end 104a, a proximal luer 108 containing the proximal end 104b, and an internal lumen 104c extending proximal of the distal end 104a and terminating within the luer 108. The lumen can be defined by a tubular support, such as a polymeric and/or braided construction, and can be configured for the passage of guidewires, microcatheters, stent retrievers, and other such devices therethrough. The lumen can also direct aspiration from the proximal end 104b to the distal tip 112 of the inner funnel catheter. The inner funnel catheter 104 can also have a rapid exchange shaft or guidewire extending proximal to the luer 108 for manipulating and delivering the inner funnel catheter 104. The distal tip 112, as show in FIG. 2, can be sized and configured such that when deployed at the target site, it expands to atraumatically contact the inner vessel walls to provide the maximum possible opening for aspirating or otherwise dislodging and receiving the clot. The expanded tip 112 can also provide flow arrest and prevent the unwanted aspiration of blood proximal to the tip 112.

The inner funnel catheter 104 can be maneuvered independent of the outer sheath 102, and vice versa. The proximal sections of the inner funnel catheter 104 can have good thrust and trackability characteristics to aid in advancing it to the target location while more distal sections can be extremely flexible for navigating tortuous anatomy. The inner funnel catheter 104 can therefore have multiple designs, or be fabricated from multiple materials, to give a reducing stiffness profile along the length to minimize insertion and retraction forces. Features can also be incorporated which bias bending about certain planes or encourage twisting for ease of delivery to a target site.

The inner funnel catheter 104 can be used in conjunction with separate mechanical devices, such as a thrombectomy device, for the removal of clots. The separate devices can be any of a number of commercially available clot retrieval products. The mechanical devices may be housed in a microcatheter which is movable relative to the inner funnel catheter 104. The microcatheter can be disposed within the lumen 104c of the inner funnel catheter. The proximal luer 108 of the inner funnel catheter can facilitate the forwarding of the microcatheter to the target site. The inner funnel catheter 104, microcatheter, and devices can be separately or simultaneously delivered to the target site through the outer sheath 102. Once the target site is reached, the tip 112 of the inner funnel catheter 104 can be expanded to the deployed state. The thrombectomy device can then be deployed from the microcatheter to engage and capture an occlusive clot while aspirating through the expanded tip 112 of the inner funnel catheter 104 and/or the outer sheath 102.

Figure 2:
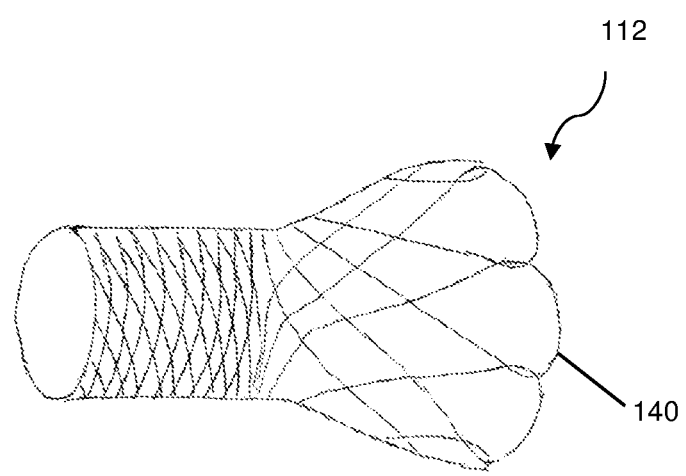
FIG. 2 is a closer view of an example of the tip of the inner funnel catheter in the deployed position according to aspects of the present invention.

As depicted in FIG. 2, the tip 112 can have a collapsed delivery configuration and a radially expanded deployed configuration in which the tip assumes a substantially conical or funnel shape. The tip 112 can be comprised of a number of struts 140. In the collapsed state, the tip 112 can have a radial dimension less than a maximum radial dimension of the tip. When deployed, the tip 112 can first extend distal to the outer sheath 102 and then grow radially outward, with at least a portion of the tip assuming a diameter greater than the diameter of the outer sheath 102. In the expanded state, the tip 112 can contact, and form a seal with, the inner wall of the vessel.

The tip 112 can be constructed from a sheet or tube stainless steel, or a superelastic shape memory alloy such as Nitinol. Alternately, the tip 112 can have a braided construction of strip or wire. The tip 112 can also be a lattice laser cut from a hypotube. The radial dimensions of the tip 112 can be sized to atraumatically contact the circumference of the inner wall of a blood vessel. The funnel shape formed by the tip 112 when expanded can improve aspiration efficiency, reduce friction, and lessen the risk of snagging on vessel openings or causing vessel trauma. The maximum radius of the tip 112 can be smaller, larger, or approximately the same size as the diameter of the target blood vessel.

The device can further have a membrane 110 (not shown) disposed radially around at least a portion of the tip 112. The same or a different membrane or membranes can also cover some or all of the longitudinal shaft of the catheter.

Figure 3A:
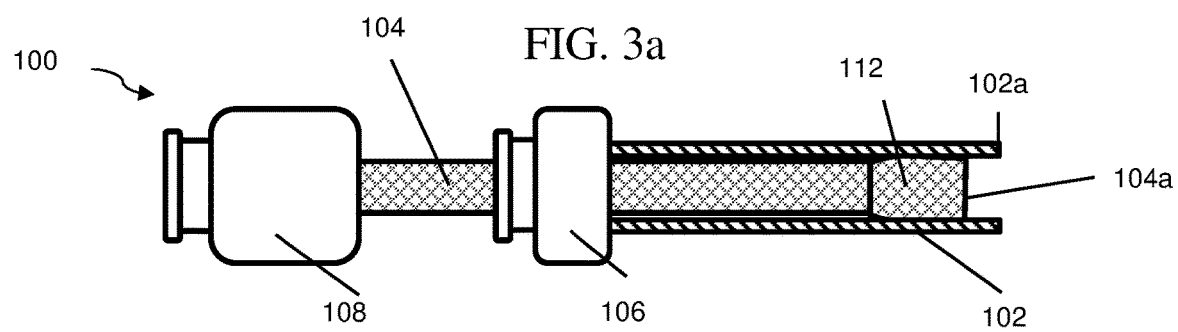
FIGS. 3a-3c are illustrations of a treatment sequence of an exemplary treatment device to retrieve a clot according to aspects of the present invention.

In FIG. 3a, the inner funnel catheter 104 is shown within the outer sheath 102, with the proximal luer 108 of the inner funnel catheter located proximally to the proximal luer 106 of the outer sheath. The inner funnel catheter 104 and the outer sheath 102 in this configuration can be provided as standalone components to be used in conjunction with one another. As an alternative, the inner funnel catheter 104 and the outer sheath 102 can be supplied pre-assembled. The inner funnel catheter 104 can be placed into to the outer sheath 102 prior to deployment of the device 100 to a target site. FIG. 3a shows the inner funnel catheter 104 with the tip 112 in the collapsed configuration constrained within the outer sheath 102. The inner funnel catheter 104 in this figure has been preloaded in a collapsed configuration, although the inner funnel catheter 104 can be preloaded in a deployed configuration as well.

Figure 3B:
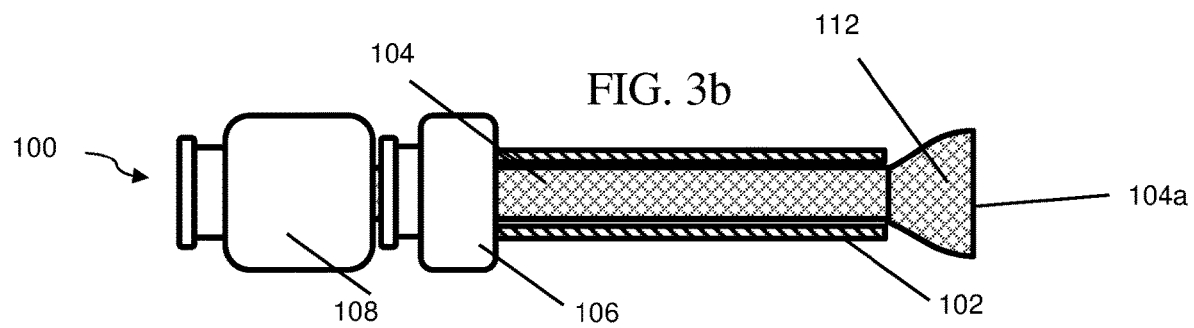

FIG. 3b depicts the proximal luer 108 of the inner funnel catheter 104, which encompasses the proximal end 104b of the inner funnel catheter, moving distally towards the proximal luer 106 of the outer sheath 102 while the proximal luer of the outer sheath 106 remains in a fixed position. This distal movement moves the inner funnel catheter 104 telescopically towards the treatment site and beyond the distal end 102a of the outer sheath. When the inner funnel catheter 104 is no longer constrained by the outer sheath 102a, the expanding distal tip 112 can deploy to facilitate removal of a clot via aspiration and/or another medical device delivered via microcatheter (not shown). The expanded funnel tip 112 can be configured to self-size in an atraumatic manner in a distally tapering blood vessel when being advanced distally of the outer catheter tip to the target treatment location.

The tip provides a large distal mouth for aspirating the clot and can be sized to be nearly the same or just larger in diameter than the target vessel. The tip 112 can thus seal with the vessel or create enough of a restriction such that when aspiration is applied, blood and the clot distal of the mouth will be drawn into the inner funnel catheter 104 rather than blood proximal of the tip. If the expanded tip 112 does not seal, or no other seal exists between the outer or clot retrieval catheter and the inner wall of the vessel, then the suction applied to the clot can be ineffective as the less restricted flow proximal of the tip would dominate.

Alternatively, in FIG. 3b, the inner funnel catheter 104 can remain in a fixed location while the proximal luer of the outer sheath 106 is moved proximally towards the proximal luer of the inner funnel catheter 108, retracting the outer sheath 102 and exposing the inner funnel catheter 104 to deploy the expanding distal tip 112. This configuration can be more atraumatic as further distal advancement of the deployed funnel is not required and a fully expanded funnel does not need to be advanced distally through a blood vessel.

Figure 3C:
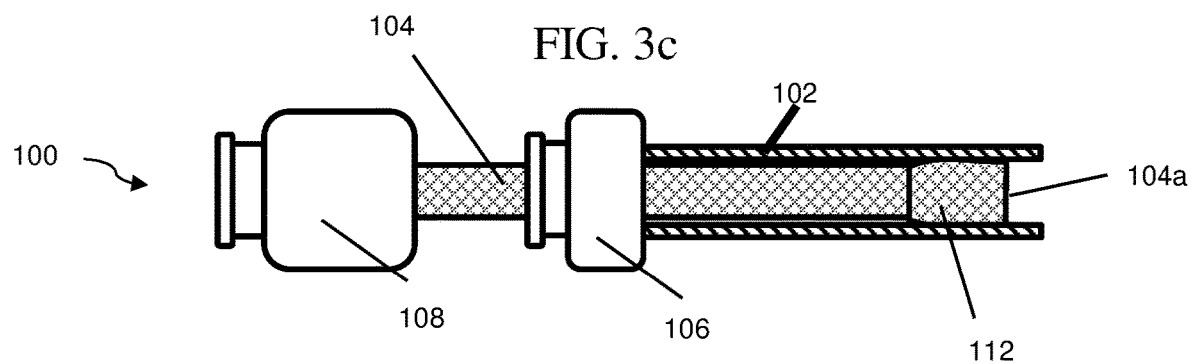

In FIG. 3c, the proximal luer 108 of the inner funnel catheter 104 is moved proximally away from the static proximal luer of the outer sheath 102, causing the inner funnel catheter 104 to move proximally back inside the outer sheath 102 and the expandable distal tip 112 to be constrained back to the collapsed configuration. For situations where a firm or fibrin-rich clot is lodged in the tip, a complete re-sheathing of the tip may not be possible and the outer sheath 102 and inner funnel catheter 104 can be withdrawn in tandem.

Figure 4A:
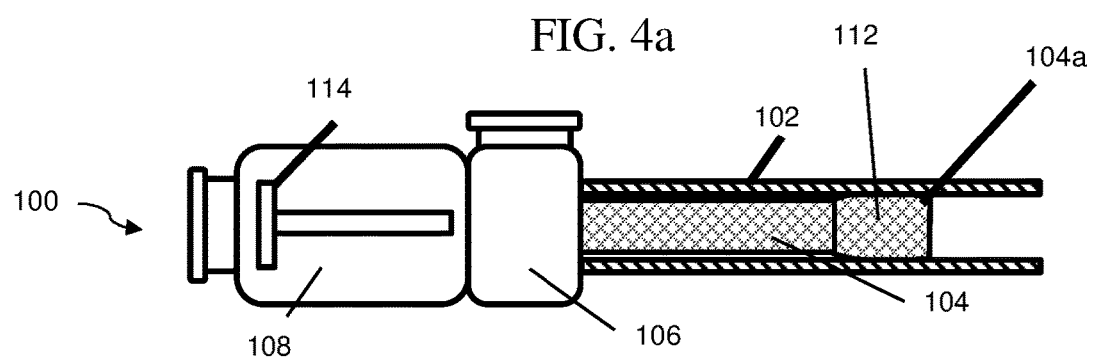
FIGS. 4a-4c shows another treatment sequence of an exemplary treatment device to retrieve a clot according to aspects of the present invention.
Figure 4B:
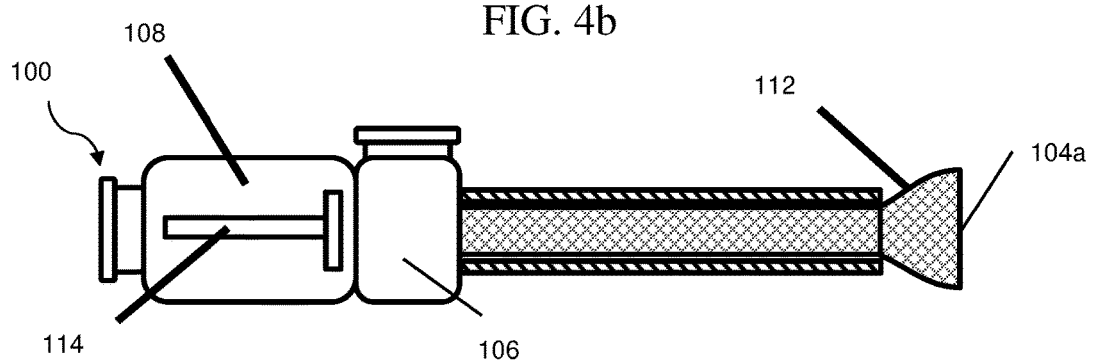
Figure 4C:
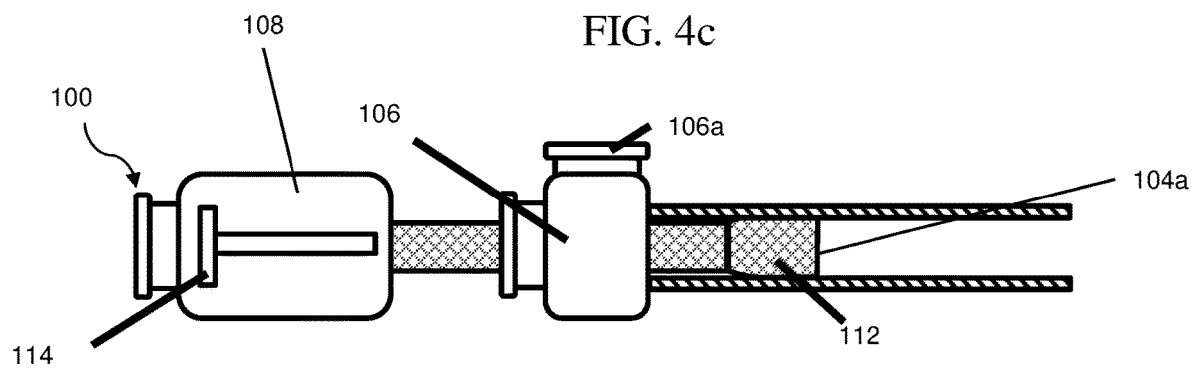

FIGS. 4a-4c depict an example of the device 100 wherein a sliding mechanism 114 is located on the proximal luer 108 of the inner funnel catheter 104 to facilitate movement of the inner funnel catheter relative to the outer sheath 102. In FIG. 4a, the proximal luer 108 of the inner funnel catheter is connected to the proximal luer 106 of the outer sheath. The proximal luer 108 of the inner funnel catheter and the proximal luer 106 of the outer sheath can be locked together for advancement through the vasculature prior to the administration of the device 100 to the treatment site. The connection between the luers may be accomplished, for example, by snap fit features, luer lock threads, a locking tab, or other suitable joining mechanisms. In the connected configuration, the proximal luer 106 of the outer sheath is located distally to the proximal luer 108 of the funnel catheter. In FIG. 4a, the expandable distal tip 112 of the inner funnel catheter 104 is in the collapsed form inside the outer sheath 102 for delivery.

The sliding mechanism 114 of the proximal luer 108 of the funnel catheter 104 can interact with the proximal end 104b of the inner funnel catheter to telescopically advance or retract the position of the funnel catheter relative to the outer sheath 102. In FIG. 4b, the slider mechanism 114 is depicted as having been moved distally across the proximal lure 108 of the inner funnel catheter, thereby moving the inner funnel catheter 104 to extend past the distal end 102a of the outer sheath and causing the distal tip 112 to deploy to the expanded configuration.

As depicted in FIG. 4c, the inner funnel catheter 104 may be withdrawn into the outer sheath 102 by retracting the slider mechanism 114 and maintaining the proximal luer 106 of the outer sheath in a fixed position while detaching and withdrawing proximally the proximal luer 108 of the inner funnel catheter. The inner funnel catheter 104 may be removed while the outer sheath 102 stays in place in the patient. If the inner funnel catheter 104 is removed, the outer sheath 102 can serve as an aspiration catheter or can maintain access to the target site for the inner funnel catheter 104 or other devices to be reinserted later. For example, if the lumen 104a of the inner funnel catheter is blocked by a captured clot, the outer sheath can remain in place while the inner funnel catheter is cleaned.

At least one hemostasis valve (not shown) can be attached to the inner funnel catheter 104 or its luer 108 and/or the outer sheath 102 and its luer 106. The proximal luer of the outer sheath 106 can also contain a side luer or port 106a for flushing. Additionally, a loading tool can be supplied to aid in re-advancing the inner funnel catheter 104 through the outer sheath 102 if the inner funnel catheter is replaced after removal. The loading tool can incorporate a split or semi-split design so that it can be peeled on or off the inner funnel catheter 104.

Figure 5A:
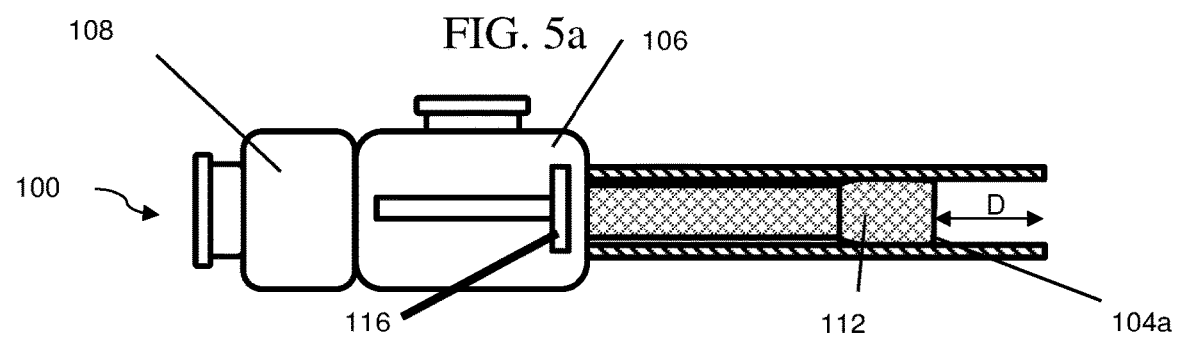
FIGS. 5a-5c are views of another treatment sequence of an exemplary treatment device to retrieve a clot according to aspects of the present invention.
Figure 5B:
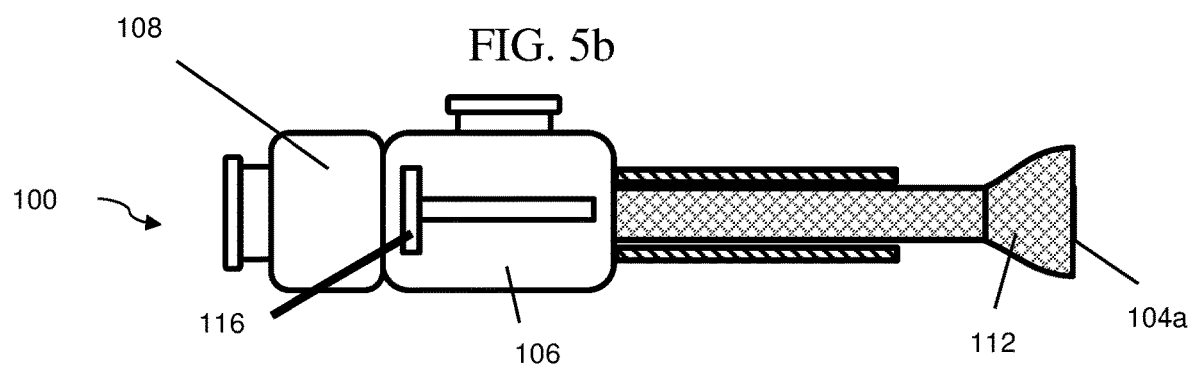
Figure 5C:
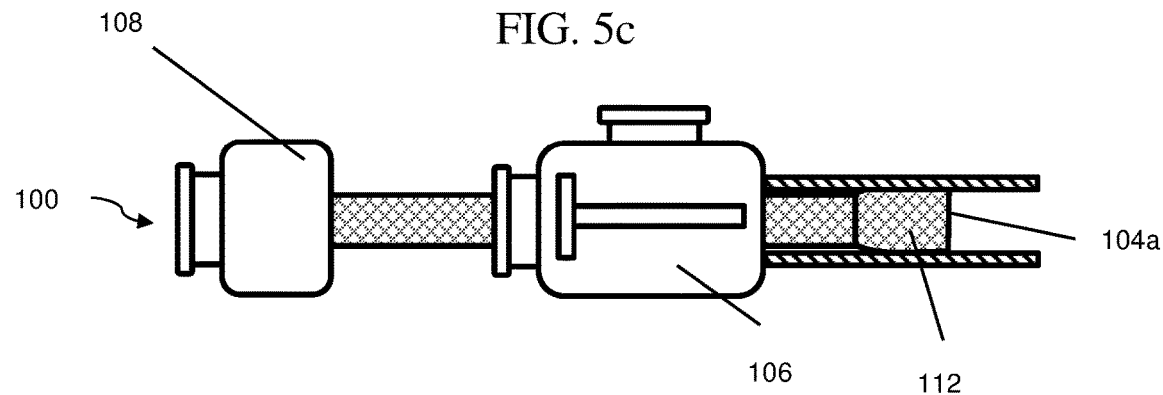

FIGS. 5a-5c depict an example of the device 100 wherein a sliding mechanism 116 is located in or on the proximal luer 106 of the outer sheath 102 to facilitate movement of the outer sheath relative to the inner funnel catheter 104. In FIG. 5a, the proximal luer 108 of the inner funnel catheter is connected to the proximal luer of the outer sheath 106. The proximal luer 108 of the inner funnel catheter and the proximal luer 106 of the outer sheath can be connected prior to advancement of the device 100 to the treatment site. As with other examples, the connection can be snap fit features, luer lock threads, a locking tab, or other joining mechanisms. In the connected configuration, the proximal luer of the outer sheath 106 is located distally to the proximal luer of the funnel catheter 108. In FIG. 5a, the distal tip 112 of the inner funnel catheter 104 is in the collapsed form inside the outer sheath 102.

The sliding mechanism 116 of the proximal luer 106 of the outer sheath 102 can advance or retract the position of the outer sheath relative to the inner funnel catheter 114. During delivery, the distal tip 112 can be in a collapsed delivery position relative to the distal end 102a of the outer sheath 102. In one example, the distance D between the distal end of the outer sheath 102a and the distal end of the inner funnel catheter 104a can be close to zero so that minimal movement is required to deploy the inner funnel catheter. In another example, the distance D for the delivery position between the distal end of the outer sheath and the distal end of the inner funnel catheter can be approximately 1 to 100 mm to maintain distal flexibility of the outer sheath. Alternatively, the distance between the distal end of the outer sheath and the distal end of the inner funnel catheter can be approximately 20 to 50 mm so that the flexibility of the outer sheath is maintained for that distance.

As depicted in FIG. 5b, by retracting the slider mechanism 116 proximally across the proximal luer of the outer sheath 106, the distal tip 112 of the inner funnel catheter 104 can be exposed outside the outer sheath 102 at a target side as the outer sheath moves proximally relative to the inner funnel catheter 104. The slider mechanism 116 can interact with a pulley pull wire set or similar articulation mechanism in the funnel catheter luer 108. The slider mechanism 116 can also be advanced distally across the outer sheath's proximal luer 106 to re-sheath the distal end 104*a* of the funnel catheter and collapse the distal tip 112 of the inner funnel catheter 104.

The configuration of FIG. 5*b* allows for the inner funnel catheter 104 to be deployed in situ, which improves deployment accuracy relative to the target site and can create a more atraumatic vessel interaction as the expanding tip 112 is not advanced distally towards the target site.

FIG. 5*c* depicts that the inner funnel catheter 104 may be withdrawn from the outer sheath 102 by maintaining the proximal luer 106 of the outer sheath in a fixed position and detaching and retracting the proximal luer 108 of the inner funnel catheter. The inner funnel catheter 104 may be removed while the outer sheath 102 remains in place, allowing the outer sheath 102 to serve as an aspiration catheter and maintain access to the target site. The proximal luer 106 of the outer sheath can also contain a side luer 106*a* for flushing.

Figure 6A:
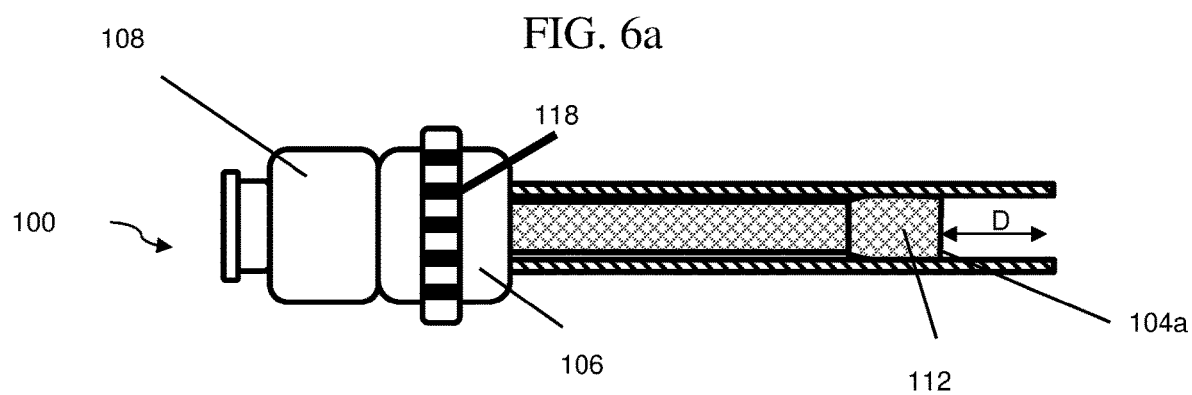
FIGS. 6a-6c depict another treatment sequence of an exemplary treatment device to retrieve a clot according to aspects of the present invention.
Figure 6B:
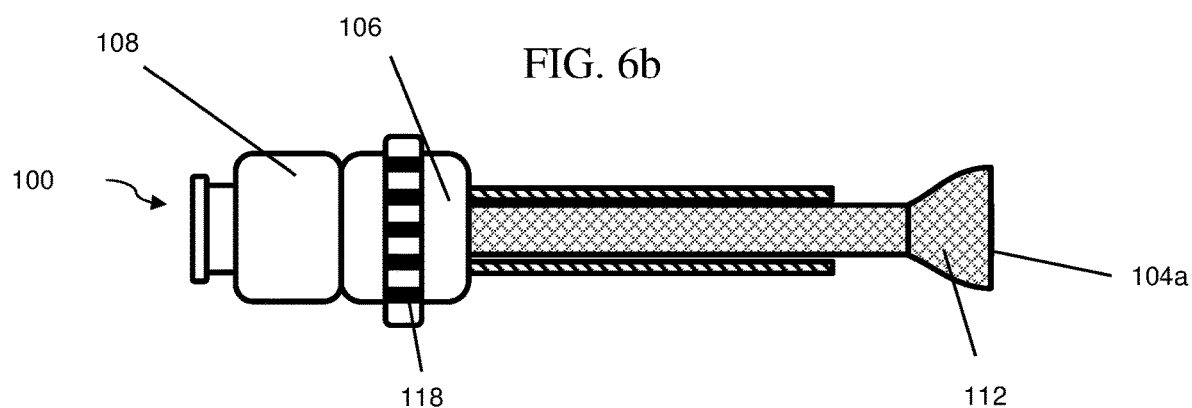
Figure 6C:
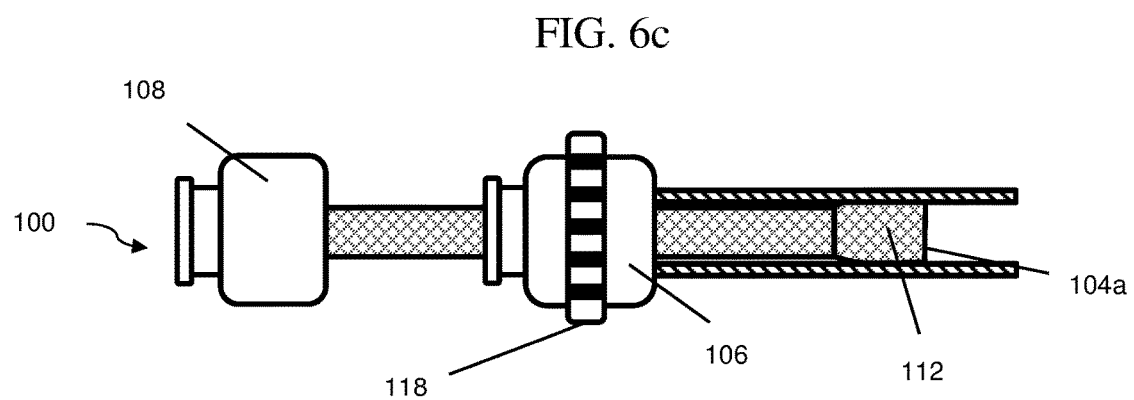

FIGS. 6*a*-6*c* depict an example of the device 100 wherein a rotating knob 118 is located on the proximal luer of the outer sheath 106 to facilitate movement of the outer sheath 102 relative to the inner funnel catheter 104. In FIG. 6*a*, when the knob 118 is rotated, the knob can interact with the proximal end 102*b* of the outer sheath 102 to telescopically advance distally or retract proximally the outer sheath relative to the inner funnel catheter 104. It is appreciated that a rotating luer set-up can also be used on the luer of the inner funnel catheter to extend or shorten its length relative to the outer sheath.

The use of a knob 118 mechanism can minimize the length of the luer 106 for devices that include a long travel between the inner and outer catheters. The overall length of the device 100 should be in the range of commonly available catheters such that the device 100 can be used with commonly available balloon guides, intermediate catheters, microcatheters, and like devices. For example, for use with balloon guides the device 100 can measure approximately 80 to 100 cm in length. For use with intermediate catheters, the device 100 can measure approximately 120 to 140 cm in length. For use with microcatheters, the device 100 can measure between 130 and 160 cm in length. Similarly, other lengths can be anticipated depending on the nature of the procedure.

The inner funnel catheter luer 108 can contain a port for connecting a syringe or another fluid or vacuum source. A plurality of channels can be provided between the outer sheath luer 106 and the funnel catheter luer 108 so that both the inner funnel catheter 104 and the outer sheath 102 may be flushed simultaneously via fluid injected into to the port of the inner funnel catheter 104.

As depicted in FIG. 6*b*, rotating the knob 118 can retract the outer sheath 102 to uncover the inner funnel catheter 104 at a target site. The outer sheath 102 can move proximally relative to the inner funnel catheter 104 through the rotating knob mechanism 118, allowing deployment of the inner funnel catheter. The knob mechanism 118 can also be rotated in the opposite direction to re-encompass the distal end 104*a* of the funnel catheter and re-sheath the expanding tip 112 of the inner funnel catheter 104.

FIG. 6*c* depicts that the inner funnel catheter 104 can be withdrawn from the outer sheath 102 by maintaining the proximal luer 106 of the outer sheath in a fixed position and detaching and retracting the proximal luer 108 of the inner funnel catheter. Similar to other examples, the inner funnel catheter 104 may be removed while the outer sheath 102 stays in place, to serve as an aspiration catheter and maintain access to the target site.

Figure 7A:
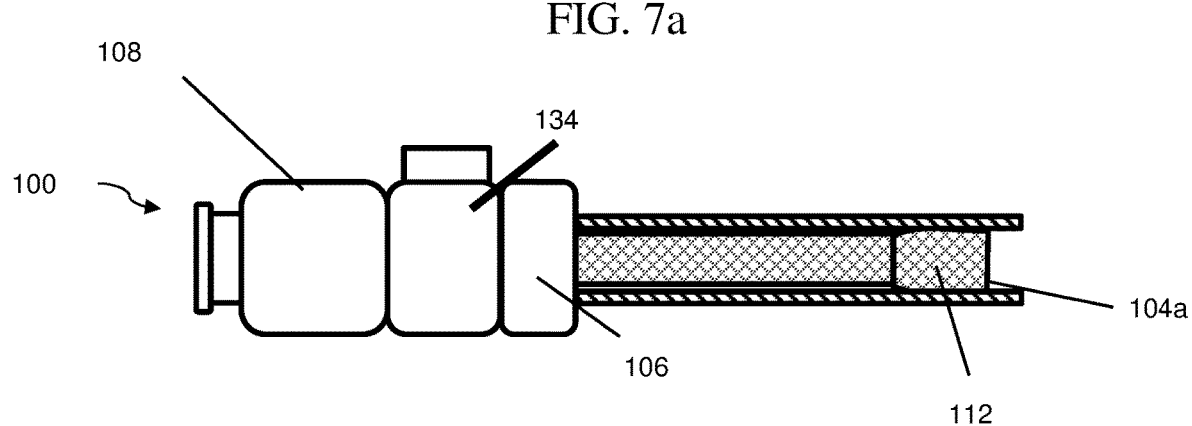
FIGS. 7a-7c illustrate another treatment sequence of an exemplary treatment device to retrieve a clot according to aspects of the present invention.
Figure 7B:
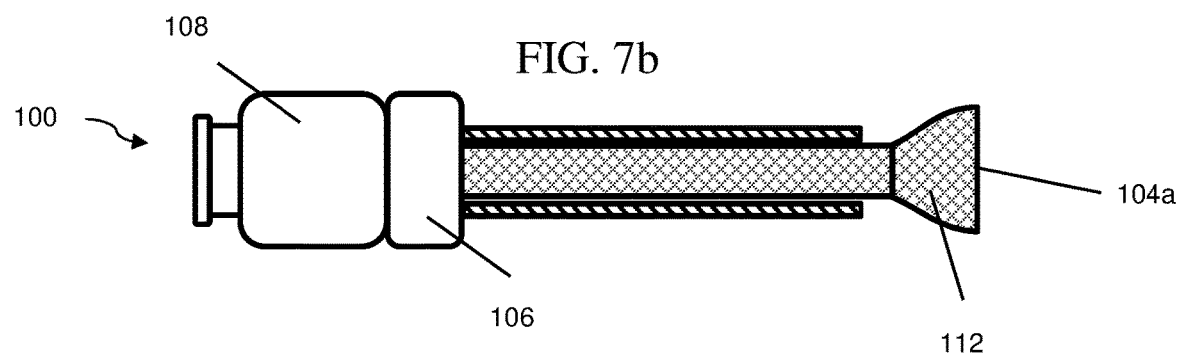
Figure 7C:
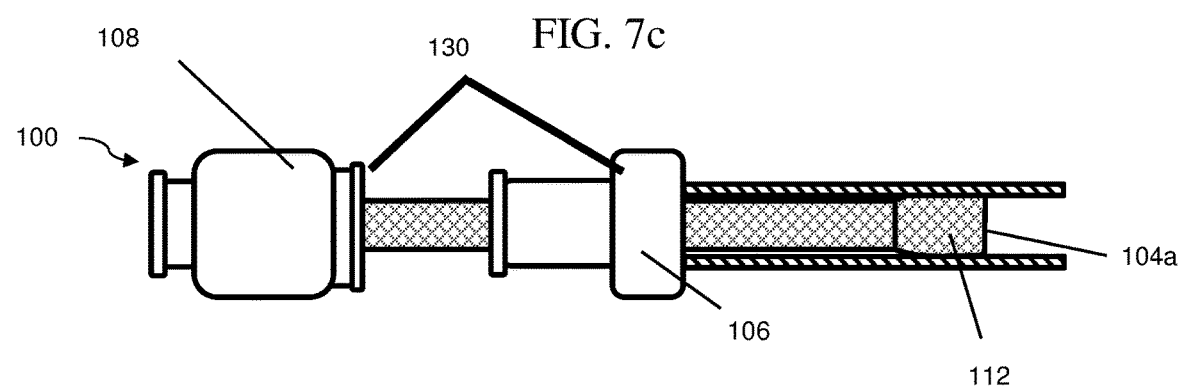

FIGS. 7*a*-7*c* depict an example of the device 100 wherein a locking tab 134 is located between the proximal luer 106 of the outer sheath 102 and the proximal luer 108 of inner funnel catheter 104. As depicted in FIG. 7*b*, the locking tab 134 can be removed. The proximal luer 106 of the outer sheath can be moved proximally towards the proximal luer 108 of the inner funnel catheter to retract the outer sheath 102 relative to the position of the inner funnel catheter 104. The locking tab 134 allows the two catheters 102, 104 to remain static relative to one another during shipping, sterilization and advancement through the vascular bed. After the locking tab has been removed, the outer sheath and inner funnel catheter can be capable of translation relative to one another. A connection mechanism can be provided to allow the luers to be temporarily connected during the procedure. This connection mechanism can include snap fit features 130 as depicted in FIG. 7*c*, luer lock threads, or other joining mechanisms. Once the clot is reached, the expanding distal tip 112 can be deployed as shown and the snap fit features 130 can lock the deployed inner funnel catheter 104 in place.

As depicted in FIG. 7*c*, the proximal luer 108 of the inner funnel catheter and the proximal luer 106 of the outer sheath can later be disconnected by overcoming the snap fit 130 force. The inner funnel catheter 104 can then be withdrawn into the outer sheath 102 by maintaining the proximal luer of the outer sheath 106 in a fixed position and detaching and retracting the proximal luer of the inner funnel catheter 108. As with other examples, at least one hemostasis valve can be attached to the inner funnel catheter 104 or its luer 108 and/or the outer sheath 102 or its luer 106.

Figure 8A:
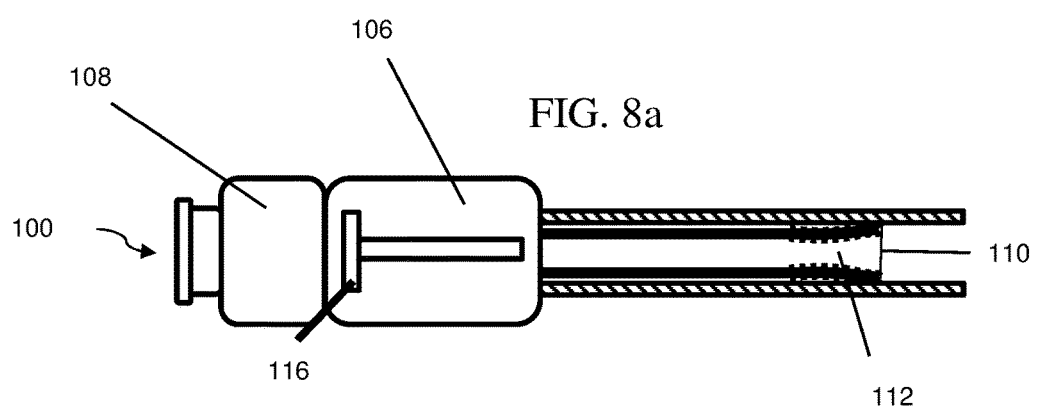
FIGS. 8a-8c show another exemplary treatment device with a membrane according to aspects of the present invention.
Figure 8B:
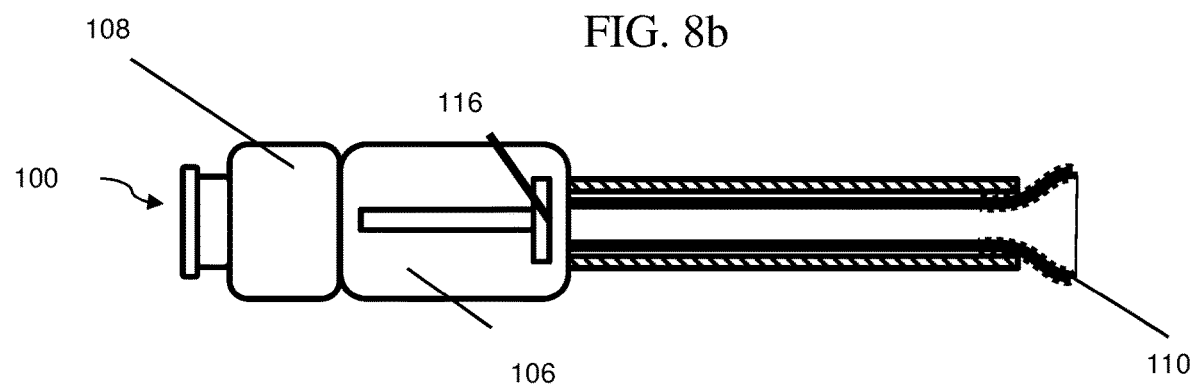
Figure 8C:
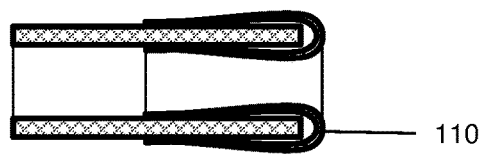

FIGS. 8*a*-8*c* are illustrations of an exemplary treatment device with a membrane according to aspects of the present invention. In some examples, the tip 112 can be overlaid by the membrane 110. When the tip 112 is fully deployed, the struts of the tip can stretch the membrane surface radially to an increased curved, funnel-like profile.

The membrane 110 can take a variety of different forms or configurations. The membrane 110 can be formed in a tubular profile with a highly elastic material such that the expanding of the tip 112 will impart a sufficient radial force to stretch the membrane 110 to the profile of the tip 112 when unconstrained. The membrane 110 can be, for example, a low-modulus elastomer. The elastomeric membrane 110 can create a gentle contact surface for sealing against the walls of the vessel when the tip 112 is deployed to the expanded configuration. In another example, the membrane 110 could be formed to include a soft elastomeric or gel rib on the outer surface to provide atraumatic contact with the vessel wall. The seal can allow for more efficient aspiration by focusing the suction distally and restricting fluid proximal of the tip, where there is no clot, from being drawn into the catheter.

If the tip 112 is cut from a hypotube, spaces, slots, or patterns can be laser-cut into the outer surface of the hypotube and the membrane 110 can be reflowed or injection molded into the spaces during manufacturing. The membrane 110 can be adhered to the struts 140 of the tip 112 using heat. Elements such as submersion dwell time, substrate withdrawal speed, temperature, humidity, and number of cycles can all be modified to give the membrane 110 a desired and uniform profile. Alternatively, a loose or baggy membrane 110 can be placed over the mouth of the tip.

As depicted in FIG. 8*a*, the membrane 110 can be attached to the expanding distal tip 112 and can also be attached to some or all of the catheter shaft proximal of the tip. The membrane may also be encapsulated over the frame in the deployed state, such that it is compressed for delivery and recovers to its original shape upon expansion. An elastomeric material may be used for the membrane 110, or a material that does not exceed its elastic strain limit when collapsed into the outer catheter.

As depicted in FIG. 8b, the membrane 110 can encapsulate the expanding tip 112 such that the membrane 100 can be stretched between the struts of the tip 112 upon expansion. Alternatively, as depicted in FIG. 8c, the membrane 110 can be formed as a tube and inverted to fold distally from inside the tip 112 and invert about the tip 112 to extend proximally along the outside surface of the tip 112. The configuration depicted in FIG. 8c does not fully encapsulate the tip 112 interstitially and therefore allows the structure of the tip 112 to expand freely within the membrane cover 110. The membrane configuration depicted in FIG. 8c thereby reduces the strain required to expand the membrane and reduces the radial force required by the tip 112 to expand.

Figure 9A:
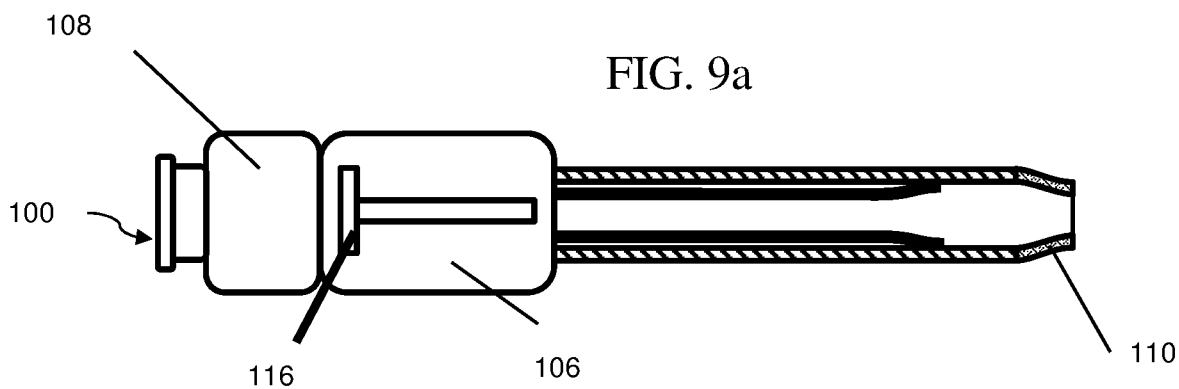
FIGS. 9a-9b are illustrations of another exemplary treatment device with a membrane according to aspects of the present invention.
Figure 9B:
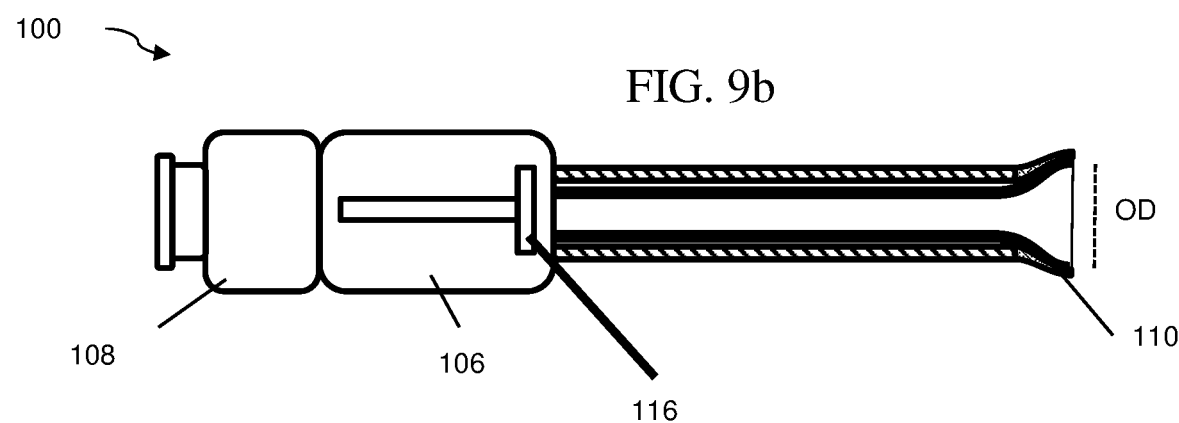

FIGS. 9a-9b are illustrations of another exemplary treatment device with a membrane according to aspects of the present invention. In FIG. 9a, the membrane 110 can be attached to the distal end of the outer sheath 102a. The membrane can have a tapered or reduced outer diameter OD which aids with advancing the device 100 atraumatically through the vasculature. The device 100 can be operated to move the inner funnel catheter 104 distally relative to the outer sheath 102, or the outer sheath 102 proximally relative to the inner funnel catheter 104, in any manner that deploys the expandable tip 112 of the inner funnel catheter just proximate a target site in accordance with FIGS. 3a-3c, 4a-4c, 5a-5c, 6a-6c, or 7a-7c. FIG. 9a depicts the device in a configuration similar to that of FIGS. 5a-5c with an outer sheath mechanism slider 116. By utilizing the slider mechanism 116, the inner funnel catheter 104 can be moved distally to press into the membrane 110, or the outer sheath 102 can be moved proximally relative to the inner funnel catheter 104. When unconstrained, the tip 112 flares into the membrane 110 and expands, causing the membrane 110 to expand in turn as seen in FIG. 9b. The membrane 110 can be elastomeric or baggy as described above.

Figure 10A:
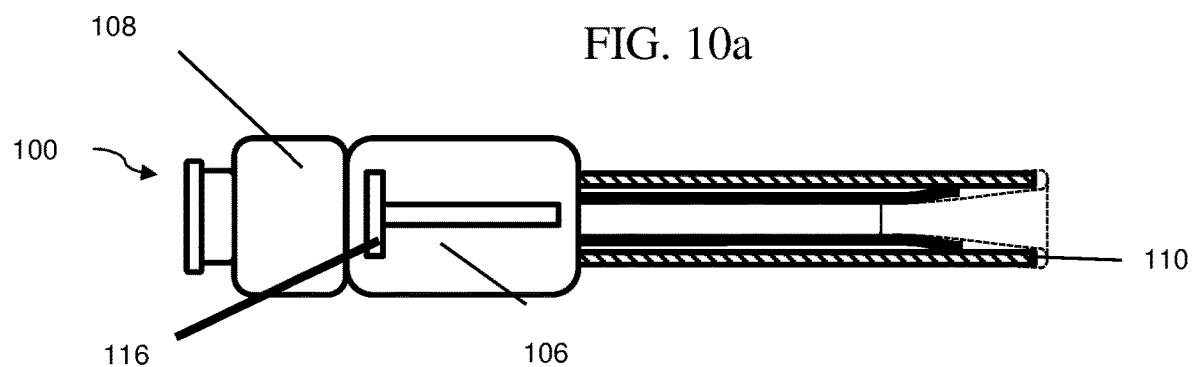
FIGS. 10a-10b are views of an exemplary treatment device with a membrane according to aspects of the present invention.
Figure 10B:
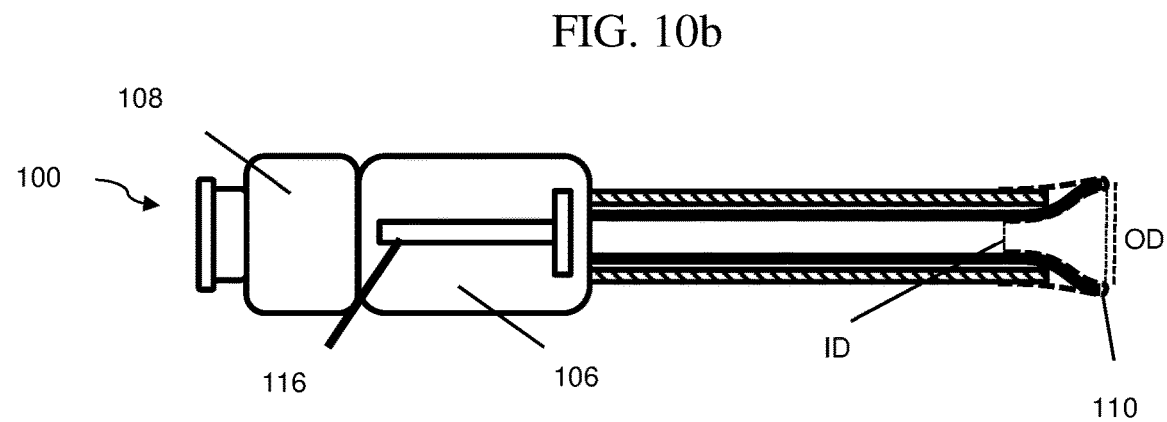

FIGS. 10a-10b are illustrations of a further exemplary treatment device with a membrane according to aspects of the present invention. In FIG. 10a, the membrane 110 is attached to the distal end of the outer sheath 102a and the inner surface of the inner funnel catheter 104. The membrane 110 is extends from an inner diameter ID of the inner funnel catheter 104 and inverts about an outer diameter OD to connect to the outer sheath 102. The device 100 can be operated to move the inner funnel catheter 104 distally relative to the outer sheath 102, or the outer sheath 102 proximally relative to the inner funnel catheter 104, in any manner that deploys the expandable tip 112 of the inner funnel catheter as with previously described examples. FIG. 10a depicts the device in a configuration similar to that of FIGS. 5a-5c with an outer sheath slider mechanism 116. When the inner funnel catheter 104 is advanced and/or the outer sheath is retracted, the membrane 110 moves with the tip 112 and expands. In the configuration shown in FIG. 10b, the outer frame of the inner funnel catheter 104 presses against the inner surface of the outer sheath 102 rather than the membrane, which reduces friction upon delivery and expansion.

Figure 11:
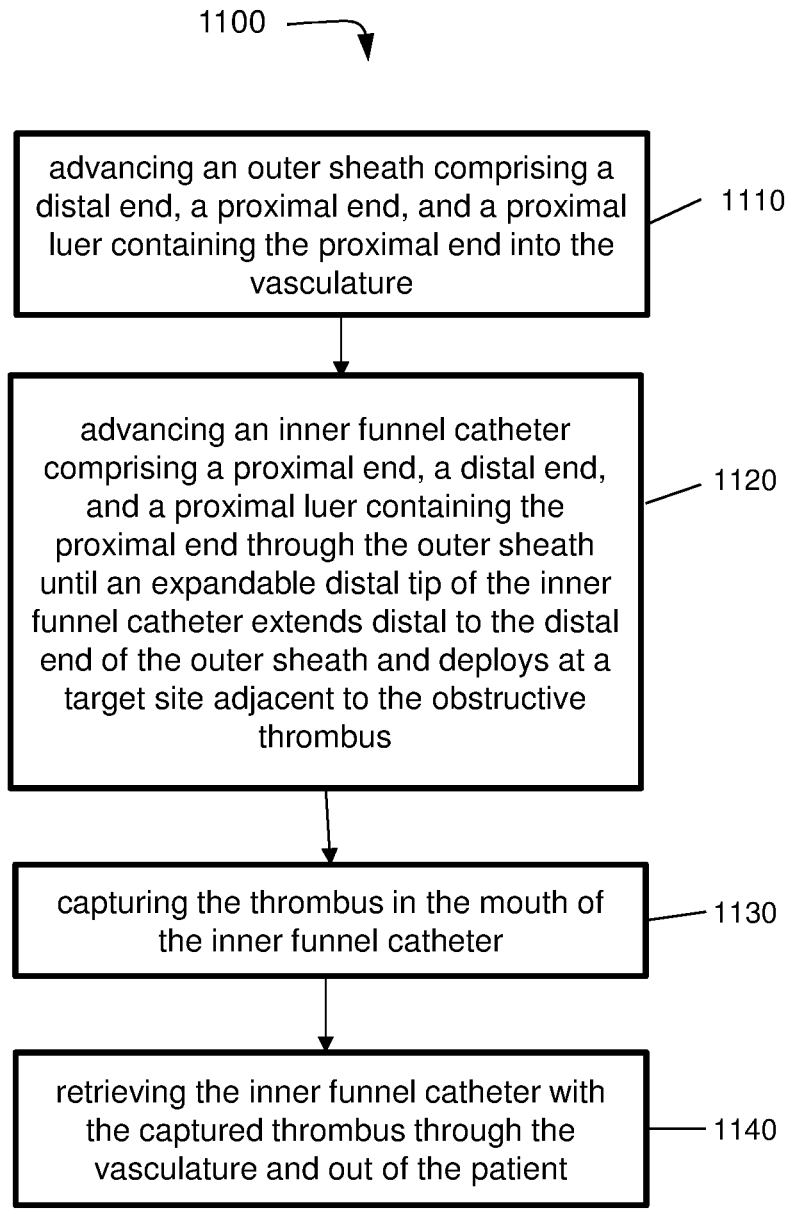
FIG. 11 is a flow diagram outlining a method of use for the device according to aspects of the present invention.

FIG. 11 depicts a flow diagram outlining a method of use of the device. The method can have some or all of the following steps and variations thereof, and the steps are recited in no particular order. The method 1100 can have the steps of advancing an outer sheath comprising a distal end, a proximal end, and a proximal luer containing the proximal end into the vasculature (1110); advancing an inner funnel catheter comprising a proximal end, a distal end, and a proximal luer containing the proximal end through the outer sheath until an expandable distal tip of the inner funnel catheter extends distal to the distal end of the outer sheath and deploys adjacent to an obstructive thrombus (1120); capturing the thrombus in the mouth of the inner funnel catheter (1130); and retrieving the inner funnel catheter with the captured thrombus through the vasculature and out of the patient (1140).

It can be appreciated that the outer sheath and inner funnel catheter can be advanced to the target site together or independently. For example, the method can involve preloading the inner funnel catheter into the outer sheath. The system can then be flushed and advanced to the target site. For ease of simultaneous advancement to the target site, a locking mechanism can hold the inner funnel catheter and outer sheath together. The mechanism can be, for example, one of a locking tab, snap fit feature, or luer lock thread. When delivered to the target site, the expandable tip of the inner funnel catheter can be deployed to expand radially in order to contact the inner walls of the blood vessel. The profile of the tip can seal against the vessel wall proximal of the target site. This seals off vessel fluid proximal to the mouth and provides a large opening to easily receive the clot.

The method can have the step of covering the expandable distal tip with a membrane. In an alternate example, advancing the tip distally can expand a membrane attached to the distal end of the outer sheath. In a further example, the membrane can be connected to the inner diameter of the funnel catheter and the outer diameter of the outer sheath.

In some examples, the step of advancing an inner funnel catheter through the outer sheath can involve moving the proximal luer of the inner funnel catheter distally towards the proximal luer of the outer sheath to advance the distal end of the inner funnel catheter towards a target site.

The outer sheath and inner funnel catheter can be moved telescopically with respect to one another by a mechanism, where the mechanism can be a slider or rotating knob. In one example, the proximal luer of the inner funnel catheter can house a slider mechanism for advancing or retracting the position of the funnel catheter relative to the outer sheath, and the method can further comprise the step of moving the slider mechanism distally across the funnel catheter's proximal luer to deploy the distal end of the funnel catheter to extend beyond the distal end of the outer sheath.

In another example, the proximal luer of the outer sheath can have the slider mechanism for advancing or retracting the position of the outer sheath relative to the inner funnel catheter, and the method can further comprise the step of retracting the slider mechanism proximally to expose and thereby deploy the tip of the inner funnel catheter beyond the distal end of the outer sheath.

In a further example, the proximal luer of the outer sheath can have a rotating knob for advancing and retracting the position of the outer sheath relative to the inner funnel catheter, and the method can further comprise the step of rotating the knob to retract the outer sheath proximally relative to the inner funnel catheter to expose the expandable tip. Re-sheathing the tip can involve the step of rotating the knob in the opposing direction.

The step of capturing the thrombus into the mouth of the clot retrieval catheter can involve using aspiration, thrombectomy devices, or other devices and practices known in the art. When the thrombus is being retrieved, the method can further have the step of maintaining the position of the outer sheath at the target site to serve as an aspiration catheter and to retain access to the target site while the inner funnel catheter and captured clot are withdrawn. Contrast media can be injected to check for vessel patency and if a blockage remains, aspiration can be directed through the outer sheath. The inner funnel catheter can also be re-advanced for aspiration. Then the outer sheath and inner funnel catheter can be removed together or independently.

In some cases, additional passes with the device may be required if the vessel is not patent. Between passes, it may be necessary to clean clot fragments and/or debris from the lumens of the inner funnel catheter and outer sheath. One or both or the proximal luers of the device can have a port for flushing, and in some cases a plurality of channels can be formed between the proximal luer of the outer sheath and the proximal luer of the inner funnel catheter. The method can then further have the step of flushing the inner funnel catheter and outer sheath simultaneously using the channels.

The invention is not necessarily limited to the examples described, which can be varied in construction and detail. The terms "distal" and "proximal" are used throughout the preceding description and are meant to refer to a positions and directions relative to a treating physician. As such, "distal" or "distally" refer to a position distant to or a direction away from the physician. Similarly, "proximal" or "proximally" refer to a position near to or a direction towards the physician. Furthermore, the singular forms "a," "an," and "the" include plural referents unless the context clearly dictates otherwise.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

In describing example embodiments, terminology has been resorted to for the sake of clarity. It is intended that each term contemplates its broadest meaning as understood by those skilled in the art and includes all technical equivalents that operate in a similar manner to accomplish a similar purpose without departing from the scope and spirit of the invention. It is also to be understood that the mention of one or more steps of a method does not preclude the presence of additional method steps or intervening method steps between those steps expressly identified. Similarly, some steps of a method can be performed in a different order than those described herein without departing from the scope of the disclosed technology. For clarity and conciseness, not all possible combinations have been listed, and such variants are often apparent to those of skill in the art and are intended to be within the scope of the claims which follow.

What is claimed is:

1. A device for retrieving an obstruction in a blood vessel, the device comprising:
   an outer sheath comprising a distal end, a proximal end, a proximal luer encompassing the proximal end of the outer sheath, and an internal lumen extending proximal of the distal end of the outer sheath and terminating within the proximal luer of the outer sheath; and
   an inner funnel catheter within the outer sheath, the inner funnel catheter comprising an expanding distal tip, a proximal end, a distal end located at the expanding distal tip, a proximal luer encompassing the proximal end of the inner funnel catheter, and an internal lumen extending proximal of the distal end of the inner funnel catheter and terminating at the proximal luer of the inner funnel catheter;
   the expanding distal tip configured to radially self-expand when unconstrained distal of the distal end of the outer sheath;
   wherein a membrane attached to an inner diameter of the inner funnel catheter and an outer diameter of the outer sheath is expanded radially by the radial self-expansion of the expanding distal tip.

2. The device of claim 1, further comprising a slider mechanism for moving the inner funnel catheter telescopically relative to a fixed position of the outer sheath.

3. The device of claim 2, wherein the slider mechanism is positioned on the proximal luer of the inner funnel catheter.

4. The device of claim 1, further comprising a rotating knob configured for moving the outer sheath telescopically relative to a fixed position of the inner funnel catheter.

5. The device of claim 1, further comprising a slider mechanism for moving the outer sheath telescopically relative to a fixed position of the inner funnel catheter.

6. The device of claim 5, wherein the slider mechanism is positioned on the proximal luer of the outer sheath.

7. The device of claim 1 further comprising a locking tab located in between the proximal luer of the inner funnel catheter and the proximal luer of the outer sheath.

8. The device of claim 1, further comprising a snap fit connection between the proximal luer of the inner funnel catheter and the proximal luer of the outer sheath.

9. The device of claim 1, wherein the expanding distal tip is at least partially encapsulated by the membrane.

10. The device of claim 1, wherein the expanding distal tip is in a collapsed delivery position within the outer sheath during advancement to the obstruction in the blood vessel.

11. The device of claim 10, wherein the collapsed delivery position of the expanding distal tip is a distance between approximately 20-50 mm proximal of the distal end of the outer sheath.

12. A method of retrieving an obstructive thrombus from a blood vessel of a patient comprising the steps of:
   advancing an outer sheath comprising a distal end, a proximal end, an internal lumen and a proximal luer containing the proximal end of the outer sheath into the vasculature;
   advancing an inner funnel catheter connected to and telescopically movable within the outer sheath, the inner funnel catheter comprising a proximal end, a distal end, an internal lumen and a proximal luer containing the proximal end of the inner funnel catheter through the outer sheath until an expandable distal tip of the inner funnel catheter extends distally to the distal end of the outer sheath and deploys at a target site adjacent to the obstructive thrombus;
   wherein the expandable distal tip is configured to radially self-expand when unconstrained distal of the distal end of the outer sheath;
   wherein a membrane attached to an inner diameter of the inner funnel catheter and an outer diameter of the outer sheath is expanded radially by the radial self-expansion of the expandable distal tip;
   capturing the thrombus in a mouth of the inner funnel catheter; and
   retrieving the inner funnel catheter with the captured thrombus through the vasculature and out of the patient.

13. The method of claim 12, further comprising maintaining a position of the outer sheath at the target site while the inner funnel catheter is retrieved.

14. The method of claim 12, further comprising moving telescopically, by a mechanism, the inner funnel catheter and the outer sheath relative to each other;
   wherein the mechanism is one of a sliding mechanism or rotating knob.

15. The method of claim 12, further comprising flushing simultaneously, by a plurality of channels formed between the proximal luer of the outer sheath and the proximal luer of the inner funnel catheter.

16. The method of claim 12, further comprising holding, by a locking mechanism, the inner funnel catheter and outer sheath together for distal advancement.

17. The method of claim 16, wherein the locking mechanism is one of a locking tab, snap fit feature, or luer lock thread.

\* \* \* \* \*